United States Patent [19]
Sullivan et al.

[11] Patent Number: 6,120,432
[45] Date of Patent: Sep. 19, 2000

[54] MEDICAL GRAFTING METHODS AND APPARATUS

[75] Inventors: Daniel J. Sullivan, Medina; Thomas J. Bachinski, Lakeville; David S. Goldsteen, Minneapolis, all of Minn.

[73] Assignee: Vascular Science Inc., Minneapolis, Minn.

[21] Appl. No.: 08/844,992

[22] Filed: Apr. 23, 1997

[51] Int. Cl.[7] ............................................. A61F 2/04
[52] U.S. Cl. ................................ 600/36; 128/898; 623/1
[58] Field of Search ........................ 128/597–98; 600/36; 606/151, 191, 108, 113, 185, 194–95; 623/1, 3, 11, 12; 604/8, 49–54, 158–59, 163–64, 272

[56] References Cited

U.S. PATENT DOCUMENTS

| | | | |
|---|---|---|---|
| 4,214,587 | 7/1980 | Sakura, Jr. | 128/334 R |
| 4,418,693 | 12/1983 | LeVeen et al. | 128/303 |
| 4,459,252 | 7/1984 | MacGregor | 264/46.9 |
| 4,503,569 | 3/1985 | Dotter | 3/1.4 |
| 4,592,754 | 6/1986 | Gupte et al. | 623/1 |
| 4,617,932 | 10/1986 | Kornberg | 128/334 R |
| 4,651,733 | 3/1987 | Mobin-Uddin | 128/303 R |
| 4,665,906 | 5/1987 | Jervis | 128/92 |
| 4,665,918 | 5/1987 | Garza et al. | 128/343 |
| 4,705,517 | 11/1987 | DiPisa, Jr. | 623/12 |
| 4,733,665 | 3/1988 | Palmaz | 128/343 |
| 4,748,984 | 6/1988 | Patel | 128/658 |
| 4,787,899 | 11/1988 | Lazarus | 623/1 |
| 4,795,458 | 1/1989 | Regan | 623/1 |
| 4,969,890 | 11/1990 | Sugita et al. | 606/192 |
| 5,035,702 | 7/1991 | Taheri | 606/153 |
| 5,061,245 | 10/1991 | Waldvogel | 604/170 |
| 5,061,275 | 10/1991 | Wallsten et al. | 623/1 |
| 5,104,399 | 4/1992 | Lazarus | 623/1 |
| 5,122,154 | 6/1992 | Rhodes | 606/198 |
| 5,147,370 | 9/1992 | McNamara et al. | 606/108 |
| 5,171,233 | 12/1992 | Amplatz et al. | 604/281 |
| 5,180,362 | 1/1993 | Worst | 604/8 |
| 5,201,901 | 4/1993 | Harada et al. | 606/198 |
| 5,209,731 | 5/1993 | Sterman et al. | 604/97 |
| 5,211,658 | 5/1993 | Clouse | 623/1 |
| 5,211,683 | 5/1993 | Maginot | 128/898 |
| 5,226,429 | 7/1993 | Kuzmak | 128/898 |
| 5,256,150 | 10/1993 | Quiachon et al. | 604/171 |
| 5,275,622 | 1/1994 | Lazarus et al. | 623/1 |
| 5,287,861 | 2/1994 | Wilk | 128/898 |
| 5,297,564 | 3/1994 | Love | 128/898 |
| 5,304,220 | 4/1994 | Maginot | 623/1 |
| 5,306,240 | 4/1994 | Berry | 604/51 |
| 5,316,023 | 5/1994 | Palmaz et al. | 128/898 |
| 5,334,217 | 8/1994 | Das | 606/213 |
| 5,354,309 | 10/1994 | Schnepp-Pesch et al. | 606/198 |
| 5,360,443 | 11/1994 | Barone et al. | 623/1 |
| 5,387,235 | 2/1995 | Chuter | 623/1 |
| 5,395,349 | 3/1995 | Quiachon et al. | 604/248 |
| 5,397,345 | 3/1995 | Lazarus | 623/1 |
| 5,409,019 | 4/1995 | Wilk | 128/898 |
| 5,419,324 | 5/1995 | Dillow | 128/653.1 |
| 5,425,765 | 6/1995 | Tiefenbrun et al. | 623/12 |
| 5,429,144 | 7/1995 | Wilk | 128/898 |
| 5,433,727 | 7/1995 | Sideris | 606/213 |
| 5,437,288 | 8/1995 | Schwartz et al. | 128/773 |
| 5,443,497 | 8/1995 | Venbrux | 623/1 |
| 5,443,499 | 8/1995 | Schmiitt | 623/1 |
| 5,451,204 | 9/1995 | Yoon | 604/1 |
| 5,452,733 | 9/1995 | Sterman et al. | 128/898 |
| 5,456,712 | 10/1995 | Maginot | 623/1 |
| 5,480,423 | 1/1996 | Ravenscroft et al. | 623/1 |
| 5,484,418 | 1/1996 | Quiachon et al. | 604/167 |
| 5,489,295 | 2/1996 | Piplani et al. | 623/1 |
| 5,496,364 | 3/1996 | Schmitt | 623/1 |
| 5,496,365 | 3/1996 | Sgro | 623/1 |
| 5,507,769 | 4/1996 | Marin et al. | 606/198 |
| 5,509,931 | 4/1996 | Schmitt | 623/1 |
| 5,522,834 | 6/1996 | Fonger et al. | 606/194 |
| 5,522,880 | 6/1996 | Barone et al. | 623/1 |
| 5,545,214 | 8/1996 | Stevens | 623/2 |
| 5,554,152 | 9/1996 | Aita et al. | 606/7 |
| 5,562,725 | 10/1996 | Schmitt et al. | 623/1 |
| 5,676,670 | 10/1997 | Kim | 606/108 |
| 5,695,504 | 12/1997 | Gifford, III et al. | 606/153 |

FOREIGN PATENT DOCUMENTS

| | | | |
|---|---|---|---|
| 670239 | 1/1994 | Australia | A61F 2/06 |
| 539237 | 4/1993 | European Pat. Off. | A61F 2/06 |
| WO 94/06372 | 3/1994 | European Pat. Off. | A61F 2/04 |
| 637454 | 2/1995 | European Pat. Off. | A61M 25/10 |
| 680734 | 11/1995 | European Pat. Off. | A61F 2/06 |
| 684022 | 11/1995 | European Pat. Off. | A61F 2/06 |
| 0 712 614 A1 | 5/1996 | European Pat. Off. . | |
| 19 54 942 | 10/1969 | Germany . | |
| 2 269 104 | 2/1994 | United Kingdom . | |
| WO 93/00868 | 1/1993 | WIPO . | |
| WO 96/01591 | 1/1996 | WIPO | A61B 17/22 |
| WO 96/01599 | 1/1996 | WIPO | A61F 2/06 |
| WO 96/18361 | 6/1996 | WIPO | A61F 2/06 |
| WO 96/22745 | 8/1996 | WIPO . | |
| WO 97/13463 | 4/1997 | WIPO | A61B 17/00 |
| WO 97/13471 | 4/1997 | WIPO | A61B 19/00 |

*Primary Examiner*—John P. Lacyk
*Attorney, Agent, or Firm*—Fish & Neave; Robert R. Jackson

[57] ABSTRACT

Methods and apparatus for delivering and installing a new length of tubing between two sections of a patient's existing body organ tubing and at least partly outside of that existing structure. For example, the new length of tubing may be for the purpose of providing the patient with a coronary bypass. The new tubing may be an artificial graft, a natural graft (harvested elsewhere from the patient), or both. The new tubing is delivered to and installed at the operative site primarily by working through the patient's existing tubular body organ structure. This avoids the need for any significant surgery on the patient.

24 Claims, 21 Drawing Sheets

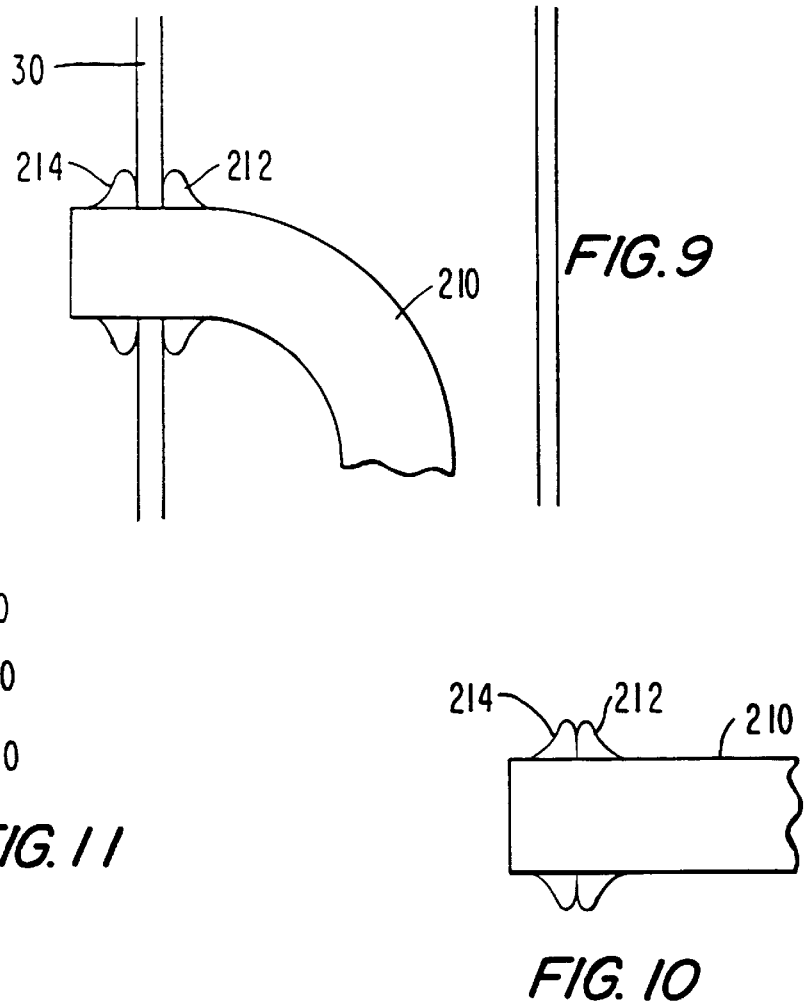

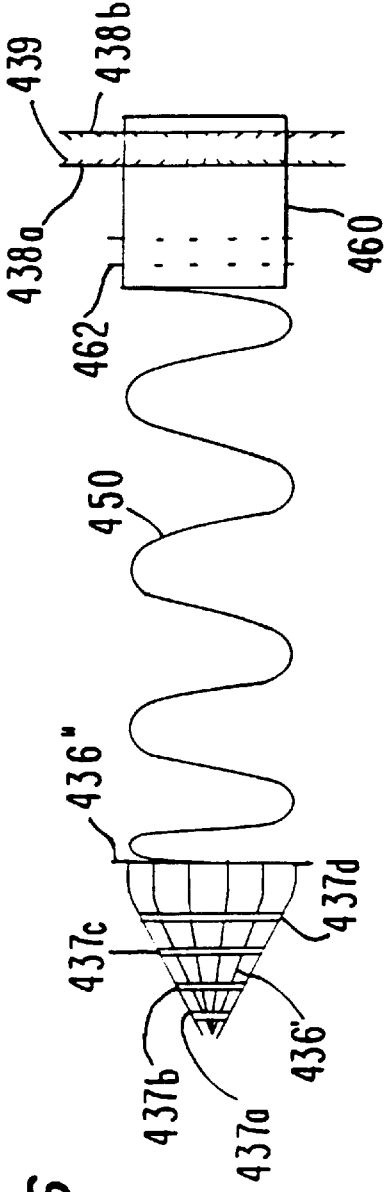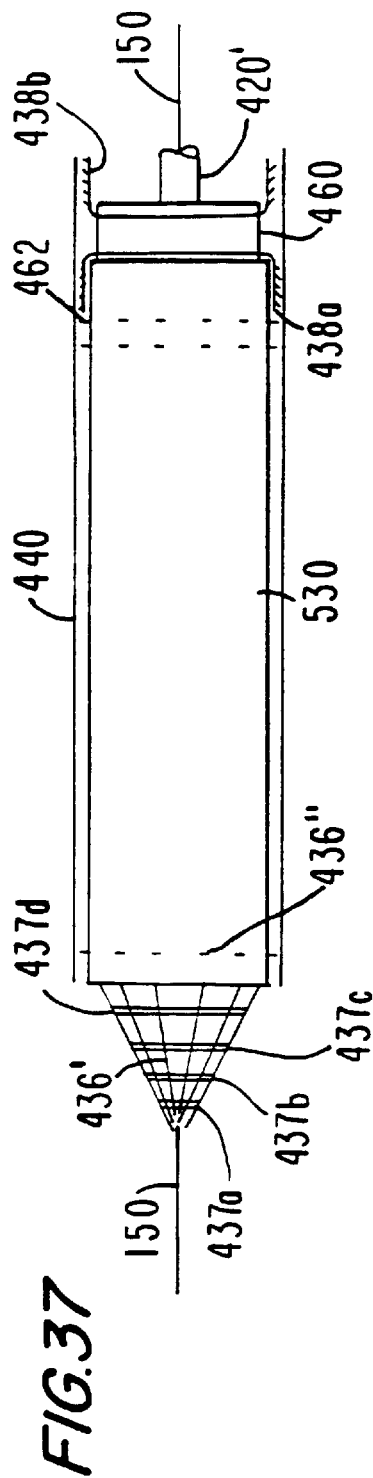

MEDICAL GRAFTING METHODS AND APPARATUS

BACKGROUND OF THE INVENTION

This invention relates to medical grafting methods and apparatus, and more particularly to methods and apparatus for installing tubular bypass grafts intralumenally.

Goldsteen et al. U.S. patent application Ser. No. 08/745,618, filed Nov. 7, 1996, shows, among other things, methods and apparatus for installing tubular bypass grafts intralumenally. (The Goldsteen et al. reference is hereby incorporated by reference herein in its entirety.) The Goldsteen et al. reference shows methods and apparatus in which each end of the graft site is approached separately and intralumenally, penetrated, and then a longitudinal structure (e.g., element 150 in the Goldsteen et al. reference) is established between the ends of the graft site. This longitudinal structure may extend intralumenally all the way out of the patient's body from both ends of the graft site. The graft is fed into the patient's body intralumenally along the longitudinal structure until it is in the desired position extending from one end of the graft site to the other. Each end of the graft is then secured at respective end of the graft site and the longitudinal structure is withdrawn from the patient.

It may not be necessary or desirable in some cases to separately approach both ends of the graft site.

It is therefore an object of this invention to provide improved methods and apparatus for intralumenal installation of bypass grafts.

It is a more particular object of this invention to provide methods and apparatus for intralumenally installing bypass grafts which do not require both ends of the graft site to be separately approached intralumenally.

SUMMARY OF THE INVENTION

These and other objects of the invention are accomplished in accordance with the principles of the invention by providing methods and apparatus for allowing a longitudinal structure to be extended intralumenally to one end of a graft site. At that end of the graft site the longitudinal structure passes out of the body structure lumen and extends extralumenally to the other end of the graft site. At the other end of the graft site, the longitudinal structure re-enters the body structure lumen. The graft is introduced intralumenally along the longitudinal structure until it passes out of the body structure lumen at the first end of the graft site and extends to the second end of the graft site. Both ends of the graft are then secured at the respective opposite ends of the graft site, and the longitudinal structure is axially withdrawn from the patient.

Further features of the invention, its nature and various advantages will be more apparent from the accompanying drawings and the following detailed description of the preferred embodiments.

BRIEF DESCRIPTION OF THE DRAWINGS

FIG. 9 is a simplified longitudinal sectional view similar to a portion of FIG. 1 showing a later stage in the illustrative procedure depicted in part by FIG. 1.

FIG. 10 is a simplified sectional view of the apparatus shown in FIG. 9 without the associated tissue structure being present.

FIG. 11 is a simplified cross sectional view of an illustrative embodiment of further illustrative apparatus in accordance with this invention.

FIG. 15b is a view similar to FIG. 15a showing more of the structure of which FIG. 15a is a part.

FIG. 36 is a simplified elevational view of apparatus which can be used as an alternative to certain apparatus components shown in FIGS. 15 and 17.

FIG. 37 is a simplified elevational view (partly in section) showing additional components with the FIG. 36 apparatus.

DETAILED DESCRIPTION OF THE PREFERRED EMBODIMENTS

Figure 1:
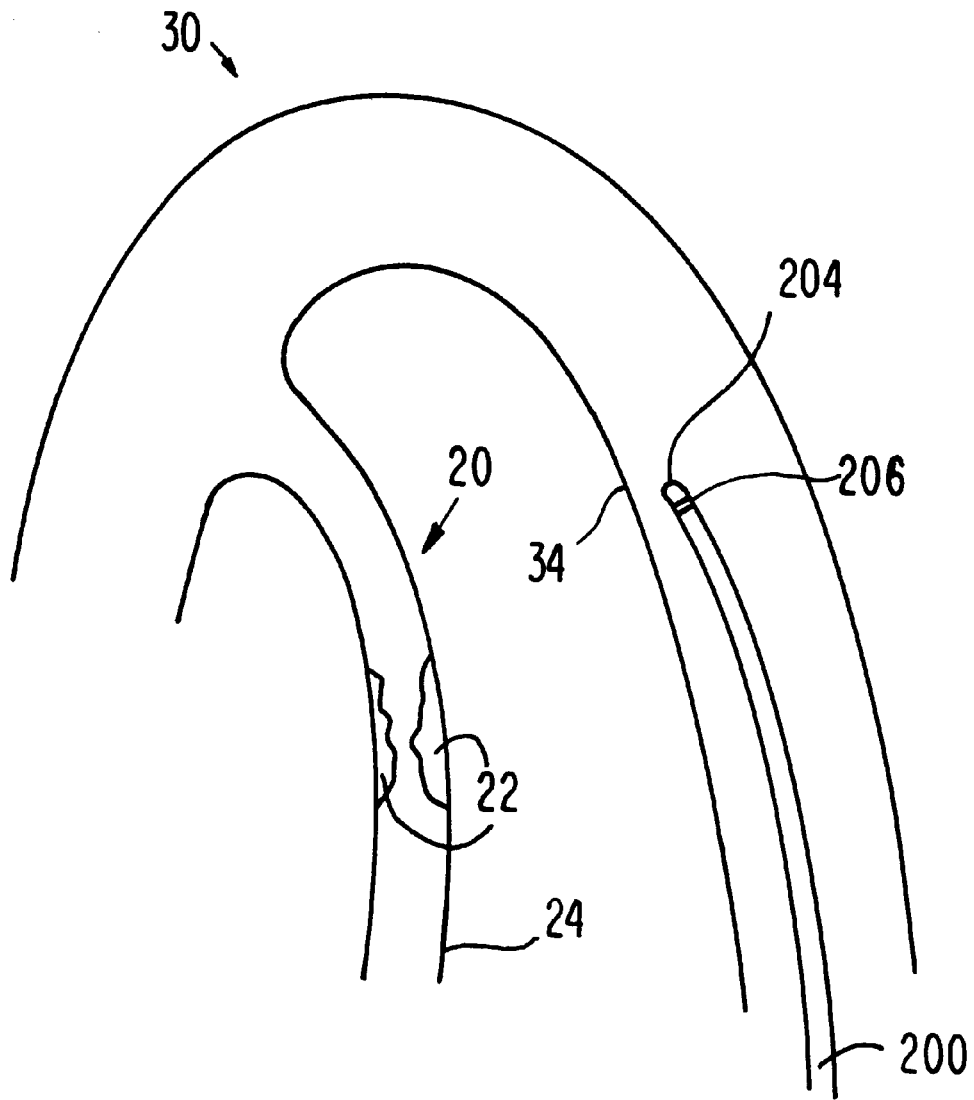
FIG. 1 is a simplified sectional view showing a portion of an illustrative procedure and related apparatus in accordance with this invention.

A typical use of this invention is to provide a bypass graft around a narrowing in a coronary artery. Thus FIG. 1 shows a patient's aorta 30 with a coronary artery 20 branching off from the aorta. A narrowing 22 in coronary artery 20 is obstructing blood flow from aorta 30 to downstream portions of the coronary artery, thereby preventing the patient's heart from receiving all the blood it needs for normal operation. To remedy this condition, a bypass graft around narrowing 22 is needed, and one way to provide such a bypass is to add a graft conduit from aorta 30 (e.g., at location 34) to a downstream portion of coronary artery 20 (e.g., at location 24).

In order to provide such a graft conduit in accordance with this invention, elongated instrumentation 200 is introduced into the patient's circulatory system, preferably from a location remote from aorta 30. For example, instrumentation 200 may be introduced into the patient's circulatory system from a femoral artery, a brachial artery, or any other suitable location. From the insertion point instrumentation 200 passes intralumenally along the patient's circulatory system until a distal portion 204 of instrumentation 200 is adjacent one end (e.g., 34) of the desired graft site. Undepicted proximal portions of instrumentation 200 always remain outside the patient adjacent the point of introduction of the instrumentation so that the physician (a term which includes any technicians or other assistants) can control the instrumentation from outside the patient's body. In particular, the depicted distal portions of instrumentation 200 are controlled remotely by the physician from outside the patient. Radiologic markers such as 206 may be provided on instrumentation 200 to aid the physician in properly locating the instrumentation in the patient.

It will be understood that the particular location 34 shown in FIG. 1 for one end of the bypass graft is only illustrative, and that any other suitable location may be chosen instead.

Figure 2:
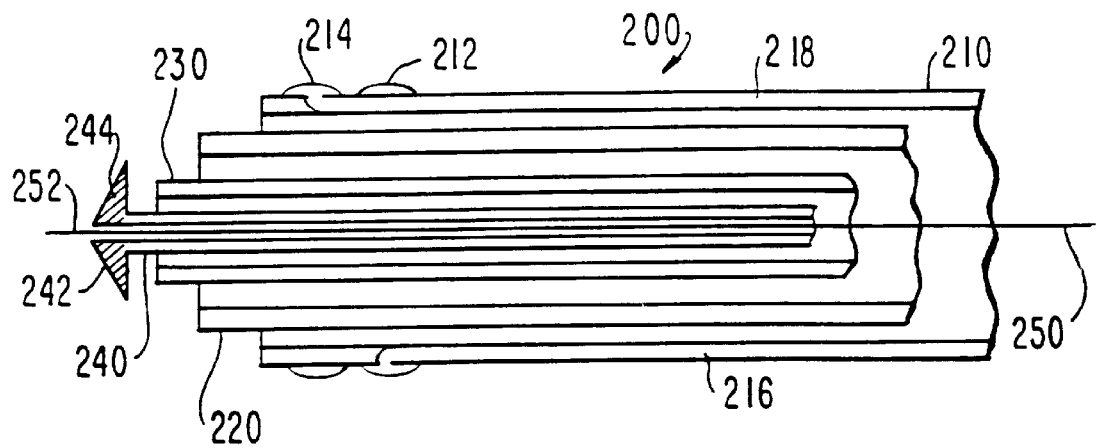
FIG. 2 is a simplified longitudinal sectional view of an illustrative embodiment of a portion of the FIG. 1 apparatus in more detail.

An illustrative construction of instrumentation 200 is shown in more detail in FIG. 2. This FIG. shows the distal portions of elements 220, 230, 240, and 250 telescoped out from one another and from the distal end of outer member 210 for greater clarity. It will be understood, however, that all of these elements are initially inside of one another and inside outer member 210. Indeed, member 210 may be initially positioned in the patient without any or all of elements 220, 230, 240, and 250 inside, and these elements may then be inserted into member 210. Moreover, the number of members like 220, 230, etc., may be more or less than the number shown in FIG. 2, depending on the requirements of a particular procedure.

Figure 4:
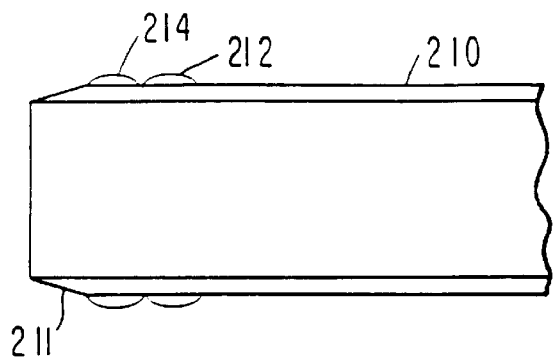
FIG. 4 is a simplified longitudinal sectional view of an alternative embodiment of one component of the FIG. 2 apparatus.

Outer member 210 may be a catheter-type member. The distal portion of catheter 210 may carry two axially spaced annular balloons 212 and 214. Proximal balloon 212 is inflatable and deflatable via inflation lumen 216 in catheter 210. Distal balloon 214 is inflatable and deflatable via inflation lumen 218 in catheter 210. Lumens 216 and 218 are separate from one another so that balloons 212 and 214 can be separately controlled. Balloons 212 and 214 are shown substantially deflated in FIG. 2. The distal end of catheter 210 may be tapered as shown at 211 in FIG. 4 to facilitate passage of catheter 210 through an aperture in aorta 30 as will be described below.

Figure 5:
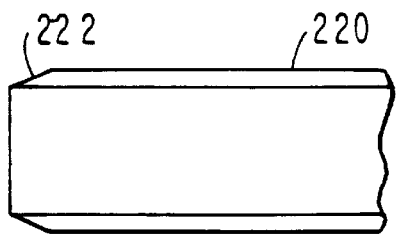
FIG. 5 is a simplified longitudinal sectional view of an alternative embodiment of another component of the FIG. 2 apparatus.
Figure 6:
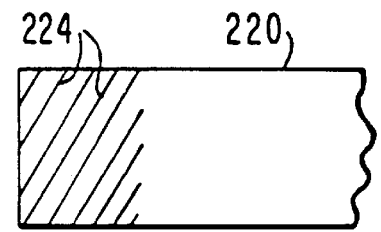
FIG. 6 is a simplified elevational view of another alternative embodiment of the component shown in FIG. 5.

Coaxially inside catheter 210 is tubular sheath member 220. Sheath 220 is longitudinally movable relative to catheter 210. The distal portion of sheath 220 may be tapered as shown at 222 in FIG. 5, and/or externally threaded as shown at 224 in FIG. 6. Either or both of features 222 and 224 may be provided to facilitate passage of sheath 220 through an aperture in aorta 30 as will be described below. If threads 224 are provided, then sheath 220 is rotatable (either alone or with other components) about the longitudinal axis of instrument 200 in order to enable threads 224 to engage the tissue of the aorta wall and help pull sheath 220 through the aorta wall.

Figure 7:
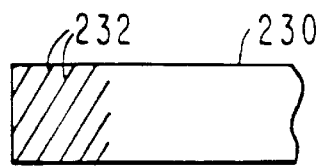
FIG. 7 is a simplified elevational view of an alternative embodiment of still another component shown in FIG. 2.

Coaxially inside sheath member 220 is power steering tube 230. Tube 230 is longitudinally movable relative to sheath 220. Tube 230 may also be rotatable (about the central longitudinal axis of instrument 200) relative to sheath 220, and the distal end of tube 230 may be threaded on the outside (as shown at 232 in FIG. 7) for reasons similar to those for which threading 224 may be provided on sheath 220. Tube 230 is preferably controllable from its proximal portion (outside the patient) to deflect laterally by a desired amount to help steer, push, or twist instrument 200 to the desired location in the patient. Examples of illustrative steering techniques are discussed in more detail below in connection with FIGS. 11–13.

Coaxially inside tube 230 is tube 240. Tube 240 is longitudinally movable relative to tube 230, and may be metal (e.g., stainless steel) hypotube, for example. Screw head 242 is mounted on the distal end of tube 240 and is threaded (as indicated at 244) on its distal conical surface. Tube 240 is rotatable (about the central longitudinal axis of instrument 200, either alone or with other elements) in order rotate head 242 and thereby use threads 244 in engagement with the tissue of the aorta wall to help pull head 242 through that wall as will be more fully described below. Because tube 240 is hollow, it can be used for passage of fluid or pressure into or out of the patient.

Figure 3:
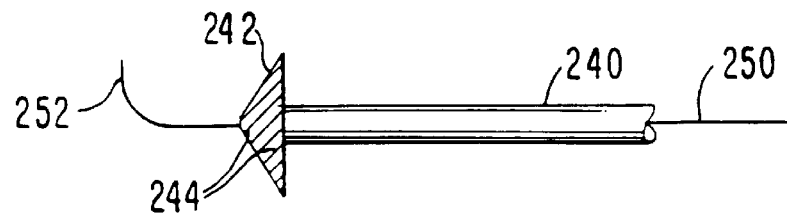
FIG. 3 is a simplified elevational view of a portion of the FIG. 2 apparatus, but with the depicted elements in a different physical relationship to one another.
Figure 8:
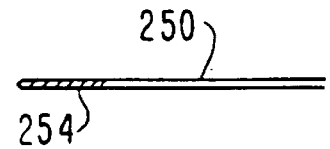
FIG. 8 is a simplified elevational view of an alternative embodiment of yet another component shown in FIG. 2.

Coaxially inside tube 240 is longitudinal structure 250. Longitudinal structure 250 is longitudinally movable relative to tube 240. Structure 250 may also be rotatable (about its longitudinal axis) relative to tube 240 and/or other elements. Structure 250 may be a wire with a distal end portion 252 that is resiliently biased to deflect laterally to one side. Wire portion 252 is kept relatively straight when it is inside tube 240 as shown in FIG. 2. But when wire portion 252 is pushed axially out the distal end of tube 240, it curves to one side as shown in FIG. 3. As an alternative or addition to the above-described resilient lateral deflection, the distal portion of structure 250 may be threaded as shown at 254 in FIG. 8 to help structure 250 thread its way through the wall of aorta 30.

All of components 210, 220, 230, 240, and 250 are controlled from outside the patient's body as is described in general terms above.

When the distal portion of catheter 210 is at the desired location 34, proximal balloon 212 is inflated. Even when inflated, proximal balloon 212 is not large enough to block aorta 30.

After proximal balloon 212 has been inflated, wire 250 is pushed distally so that its distal portion emerges from the distal end of tube 240 and penetrates the wall of aorta 30 at location 34. This anchors the distal portion of instrument 200 to the aorta wall at the desired location. Because of its operation to thus anchor instrument 200, wire 250 is sometimes referred to as an anchor wire. The rotatability of wire 250, as well as its resilient lateral deflection (FIG. 3) and/or threads 254 (FIG. 8), may be used to help get the distal end of the wire to the desired location 34 and firmly into the aorta wall at that location in order to achieve the desired anchoring of instrument 200.

When instrument 200 is sufficiently anchored by wire 250, tubes 230 and 240 are moved in the distal direction relative to wire 250 so that screw head 242 begins to follow wire 250 into and through the aorta wall. During this motion, at least tube 240 is rotated about its longitudinal axis so that threads 244 help to pull head 242 into and through the aorta wall. The distal portion of tube 230 follows head 242 through the aorta wall. If provided, threads 232 and rotation of tube 230 may facilitate transfer of the aorta wall tissue from head 242 to tube 230.

When tube 230 is through the aorta wall, sheath 220 is moved distally relative to tube 230 so that a distal portion of sheath 220 follows tube 230 through the aorta wall. If provided, the distal taper 222 and/or threads 224 and rotation of sheath 220 help the distal portion of sheath 220 through the aorta wall. Then catheter 210 is advanced distally relative to sheath 220 so that a distal portion of catheter 210 follows sheath 220 through the aorta wall. Again, the distal taper 211 of catheter 210 (if provided) helps the distal portion of the catheter through the aorta wall. Inflated proximal balloon 212 prevents more than just the portion of catheter 210 that is distal of balloon 212 from passing through the aorta wall.

It should be mentioned that each time another, larger one of elements 240, 230, 220, and 210 is pushed through the aorta wall, the previously extended elements can be and preferably are either held stationary or pulled back proximally to prevent them from damaging body tissues outside the aorta. It should also be mentioned that threading such as 254, 244, 232, and 224 is entirely optional and can be omitted if the associated elements are made sharp enough and can be pushed distally sufficiently strongly to penetrate the aorta wall without the aid of threading and rotation.

When the distal portion of catheter 210 is through the aorta wall, distal balloon 214, which is now outside the aorta, is also inflated. The axial spacing between balloons 212 and 214 is preferably small enough so that the aorta wall is clamped between these two balloons as shown in FIG. 9. For example, if balloons 212 and 214 were inflated without the presence of the aorta wall, their appearance might be as shown in FIG. 10. The close spacing of balloons 212 and 214, as well as their resilient bias toward one another, helps to anchor catheter 210 through the aorta wall and also to seal the aorta wall around the catheter. Balloons 212 and 214 may be inflated by liquid or gas, and they may be specially coated to help improve the seal between catheter 210 and the aorta wall.

After the condition of catheter 210 shown in FIG. 9 has been reached, all of components 220, 230, 240, and 250 can be withdrawn from the patient by pulling them out of catheter 210 in the proximal direction.

The next step in the illustrative procedure being described is to insert an elongated, steerable, endoscopic instrument 300 lengthwise into catheter 210. A simplified cross sectional view of an illustrative steerable endoscopic instrument 300 is shown in FIG. 11. As shown in that FIG., instrument 300 includes one or more sheath structures such as 310a and 310b that are operable by the physician to steer the instrument by curvilinearly deflecting it laterally by a desired, variable amount. In lieu of or in addition to steering sheaths 310a and 310b, any other conventional steering elements may be provided and used. Other examples of suitable steering structures are shown in Bachinski et al. U.S. patent application Ser. No. 08/842,391, filed Apr. 23, 1997 (Docket No. 293/006), which is hereby incorporated by reference herein. Within sheaths 310 are such other components as (1) a fiber optic bundle 320 for conveying light from outside the patient to the distal end of instrument 300 in order to provide illumination beyond the distal end of the instrument, (2) another fiber optic bundle 330 for conveying an image from beyond the distal end of the instrument back to optical and/or video equipment outside the patient and usable by the physician to see what is beyond the distal end of the instrument, and (3) a lumen 340 with a longitudinal structure 150 (i.e., a wire) inside of it. Additional lumens such as 360 may be provided for such purposes as (1) introducing fluid that may help to clear the distal ends of fiber optic bundles 320 and 330, (2) introducing fluid for irrigating and/or medicating the patient, (3) suctioning fluid from the patient, etc.

Figure 12:
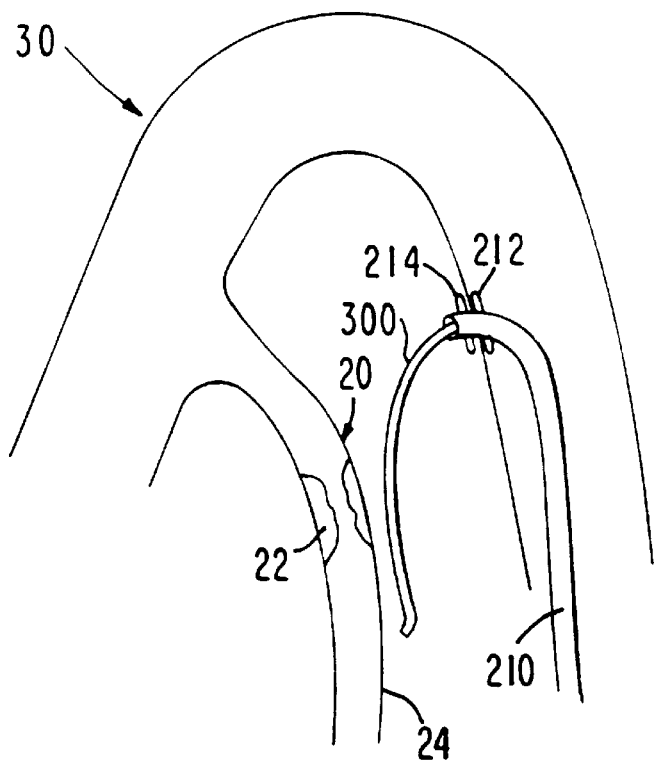
FIG. 12 is a view similar to FIG. 1 showing an even later stage in the illustrative procedure depicted in part by FIG. 9, together with related apparatus, all in accordance with this invention.

As shown in FIG. 12, the distal portion of steerable endoscopic instrument 300 is extended distally beyond the distal end of catheter 210 and steered by the physician until it is adjacent to the exterior of coronary artery portion 24. The endoscopic features of instrument 300 are used by the physician to help steer the distal end of the instrument to the desired location. Instrument 300 may also be provided with radiologic markers (like markers 206 on instrument 200 in FIG. 1) to additionally help the physician get the distal end of instrument 300 to the desired location.

Figure 13:
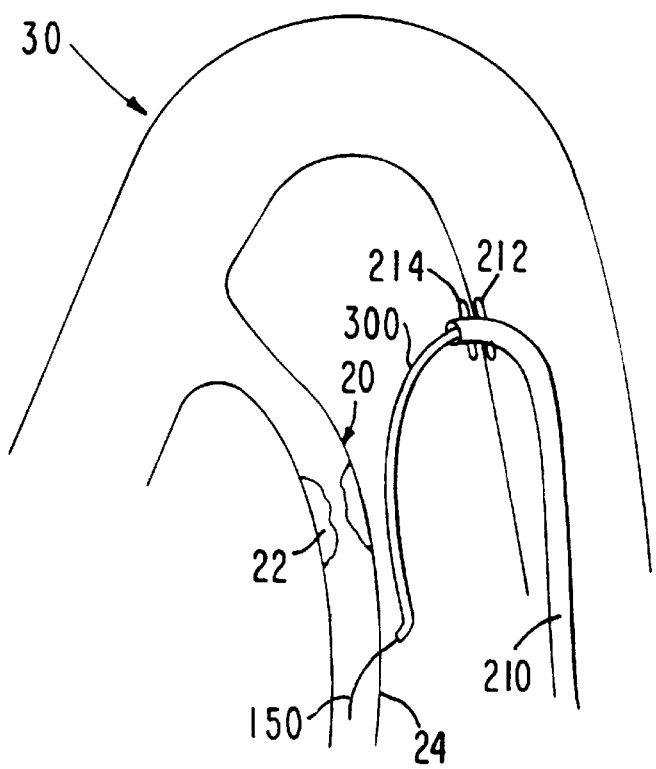
FIG. 13 is a view similar to FIG. 12 showing a still later stage in the illustrative procedure depicted in part by FIG. 12.

The next step in the illustrative procedure being described is to extend longitudinal structure 150 from the distal end of instrument 300 so that it passes through the wall of coronary artery 20 at location 24 and into the lumen of the artery as shown in FIG. 13. To facilitate penetration of the coronary artery wall, the distal end of longitudinal structure 150 may be sharply pointed. The distal portion of longitudinal structure 150 may also be threaded (analogous to the threads 254 shown on the distal portion of longitudinal structure 250 in FIG. 8) and longitudinal structure 150 may be rotated about its longitudinal axis so that the threads engage the coronary artery wall tissue and pull longitudinal structure 150 into and through the coronary artery wall. The distal portion of longitudinal structure 150 is preferably pushed sufficiently far down into the lumen of coronary artery 20 so that it does not inadvertently come out of the coronary artery.

Figure 13A:
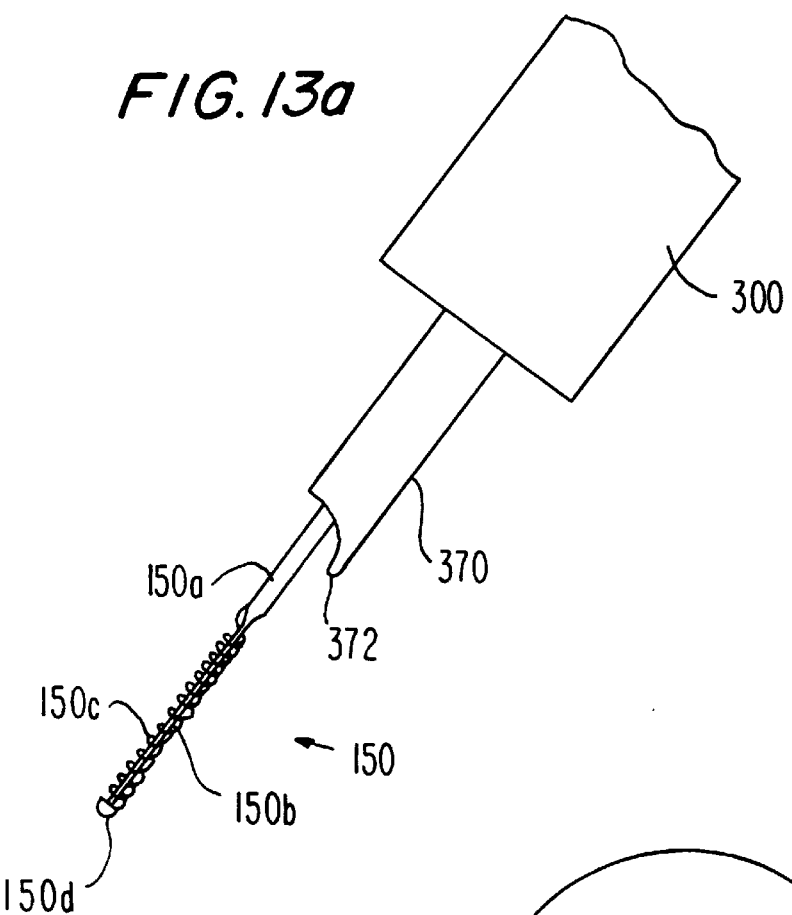
FIG. 13a is a simplified elevational view of an illustrative embodiment of structural details that can be included in apparatus of the type shown in FIGS. 11–13.

FIG. 13a shows alternative apparatus that may be used to introduce the distal portion of longitudinal structure 150 into coronary artery 20 at location 24. This apparatus includes a hypotube 370 that extends distally from the distal end of instrument 300. Hypotube 370 may have a fixed amount of extension from instrument 300, or it may be selectively extendable from instrument 300. Hypotube 370 has a sharply pointed distal tip portion 372, the purpose of which will be described below. An illustrative size for hypotube 370 is about 0.015 inches in diameter.

Longitudinal structure 150 is disposed coaxially inside hypotube 370 and is axially and rotatably movable relative to hypotube 370. The proximal portion 150a of structure 150 may be a wire having a diameter of about 0.009 inches. A distal portion 150b of wire 150a may be ground down to produce a safety ribbon inside wire coil 150c. An illustrative size for the wire of coil 150c is about 2 mils. The proximal end of coil wire 150c is secured to wire 150a. The distal end of coil wire 150c is secured to distal tip 150d, which is also secured to the distal end of safety ribbon 150b. Elements 150b, 150c, and 150d cooperate to give longitudinal structure 150 a highly flexible distal portion.

Prior to use of sharply pointed cutter tip 372 as described below, the distal portion of longitudinal structure 150 may be distally extended from the distal portion of hypotube 370. This protects cutter tip 372 and also protects nearby tissue from the cutter tip.

Instrument 300 is controlled as described above in connection with FIG. 12 to position cutter tip 372 adjacent coronary artery portion 24. Longitudinal structure 150 is then retracted proximally to expose cutter tip 372. Next, cutter tip 372 is advanced to make a slit through coronary artery portion 24. With cutter tip 372 still in this slit, longitudinal structure 150 is moved distally relative to hypotube 370 so that the distal portion of structure 150 passes through the above-mentioned slit into the lumen of coronary artery 20. Once inside the coronary artery lumen, the distal portion of longitudinal structure 150 can be pushed farther down along that lumen. Wire coil 150c can be used to threadedly engage the interior of the coronary artery where the coronary artery narrows down (farther along its length) to help releasably anchor the distal portion of structure 150 in the coronary artery. This threaded engagement can be produced by rotating longitudinal structure 150 about its longitudinal axis when the longitudinal structure begins to encounter resistance to further distal pushing along the coronary artery. Of course, this threaded engagement is reversible by rotating longitudinal structure 150 in the direction opposite to the direction which produces the threaded engagement.

Figure 14:
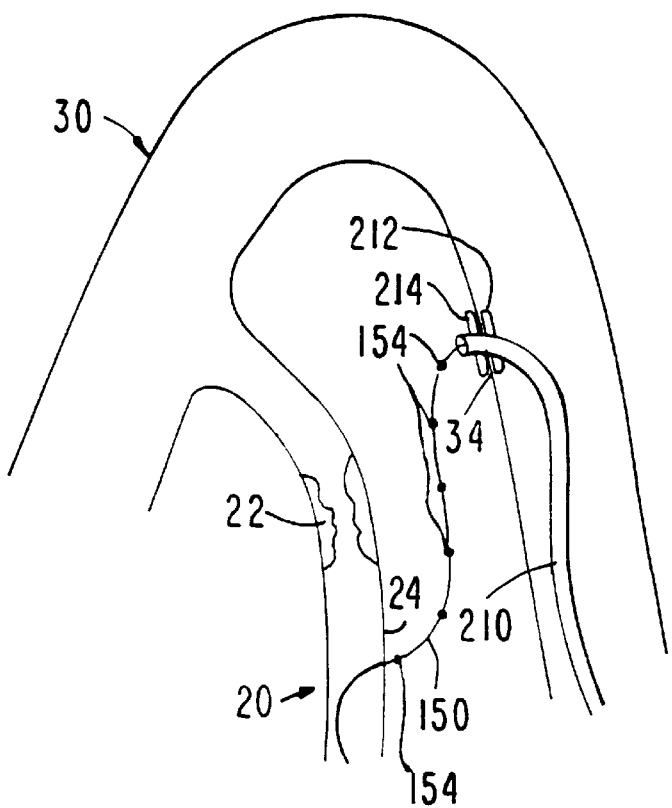
FIG. 14 is a view similar to FIG. 13 showing an even later stage in the illustrative procedure depicted in part by FIG. 13.

After the distal portion of longitudinal structure 150 is satisfactorily in place in the lumen of coronary artery 20 as described above in connection with FIG. 13 and/or FIG. 13a, the next step is to withdraw instrument 300 (including hypotube 370 if provided) from the patient by pulling instrument 300 back out through catheter 210. Only longitudinal structure 150 from instrument 300 is left in the patient as shown in FIG. 14. If desired, longitudinal structure 150 may be provided with radiologic markers 154 equally spaced along the length of its distal portion to help the physician determine by radiologic observation the actual length between location 24 and location 34. This enables the physician to determine the exact length of the graft tubing needed to connect locations 24 and 34.

The next phase of the illustrative procedure being described is to install a new length of tubing between regions 24 and 34. The new length of tubing may be either an artificial graft, natural body organ tubing harvested from the patient's body, or a combination of artificial and natural tubing (e.g., natural tubing coaxially inside artificial tubing). In the following discussion it is assumed that the new tubing is to be natural tubing (e.g., a length of the patient's saphenous vein that has been harvested for this purpose) inside an artificial conduit. When such a combination of natural and artificial conduits is used, both conduits can be delivered and installed simultaneously, or the outer artificial conduit can be delivered and installed first, and then the inner natural conduit can be delivered and installed. The following discussion initially assumes that the latter technique is employed.

Figure 15:
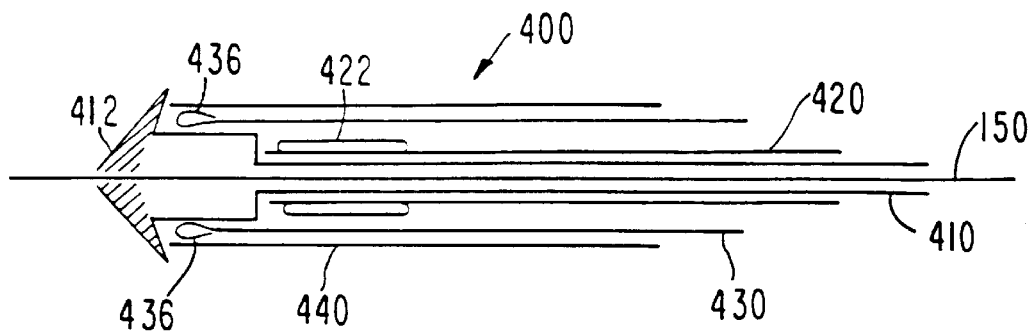
FIG. 15 is a simplified longitudinal sectional view of an illustrative embodiment of a portion of still further illustrative apparatus in accordance with this invention.

In accordance with the above-stated assumptions, the next step in the procedure is to use catheter 210 and longitudinal structure 150 (hereinafter referred to for convenience and simplicity of terminology as wire 150) to deliver an artificial conduit so that it extends between regions 24 and 34. The distal portion of an illustrative assembly 400 for doing this is shown in FIG. 15. (Several alternative constructions of this portion of the apparatus are shown in later FIGS. and described below.)

As shown in FIG. 15 assembly 400 includes a threaded, conical, distal tip 412 mounted on a tubular member 410 (e.g., metal hypotube) through which wire 150 can freely pass. Additional details regarding various possible constructions of tip 412 are provided later with reference to FIGS. 15a–15g, but it should be mentioned here that in this embodiment tip 412 is selectively collapsible to facilitate its withdrawal from the patient after it has served its purpose. Another tubular member 420 is disposed concentrically around tubular member 410. An inflatable balloon 422 is mounted on the distal end of tubular member 420. Tubular member 420 includes an axially extending lumen (not shown in FIG. 15) for use in selectively inflating and deflating balloon 422. Balloon 422 is shown deflated in FIG. 15.

Figure 16:
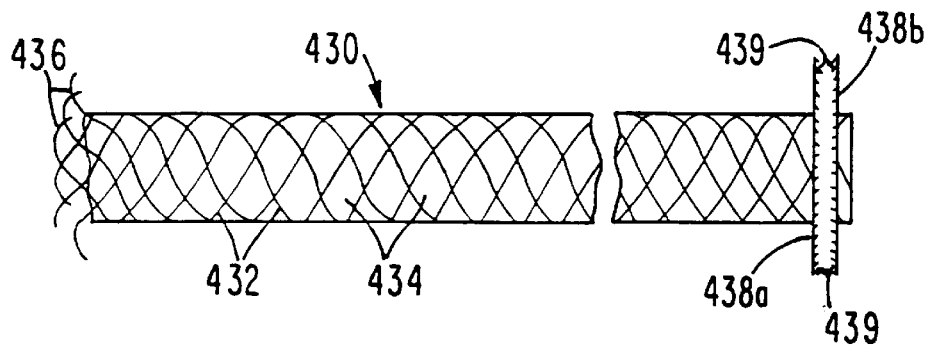
FIG. 16 is a simplified elevational view of an illustrative embodiment of one component of the FIG. 15 apparatus.

Coaxially around tubular member 420 is an artificial graft conduit 430. An illustrative embodiment of a suitable conduit 430 is shown in FIG. 16 and includes a tube formed of a frame 432 of a first highly elastic material (such as nitinol) with a covering 434 of a second highly elastic material (e.g., a rubber-like material such as silicone) substantially filling the apertures in the frame. Additional information regarding this possible embodiment of conduit 430 and other suitable artificial graft structures is provided in the Goldsteen et al. reference which is first mentioned above (see also Bachinski et al. U.S. patent application Ser. No. 08/839,080, filed Apr. 23, 1997 (Docket No. 293/005), which is also hereby incorporated by reference herein). Here it will suffice to say that this structure is extremely elastic, flexible, pliable, and resilient. For example, it can be stretched to a small fraction of its original diameter, and it thereafter returns by itself to its original size and shape without damage or permanent deformation of any kind. In addition, this structure is distensible so that it may pulsate very much like natural circulatory system tubing in response to pressure waves in the blood flow. This helps keep the conduit open, especially if it is used by itself as the final graft conduit. At its distal end, extensions of frame 432 are flared out to form resilient hooks or barbs 436, the purpose of which will become apparent as the description proceeds. Near the proximal end of conduit 430 two axially spaced resilient flaps 438a and 438b with hooks or barbs 439 are provided. The purpose and operation of elements 438 and 439 will also become apparent as the description proceeds.

In assembly 400 (see again FIG. 15, and also FIG. 17), hooks 436 and flaps 438 are compressed radially inwardly and confined within conduit delivery tube 440, which coaxially surrounds conduit 430. Indeed, conduit 430 may be somewhat circumferentially compressed by tube 440.

Figure 17:
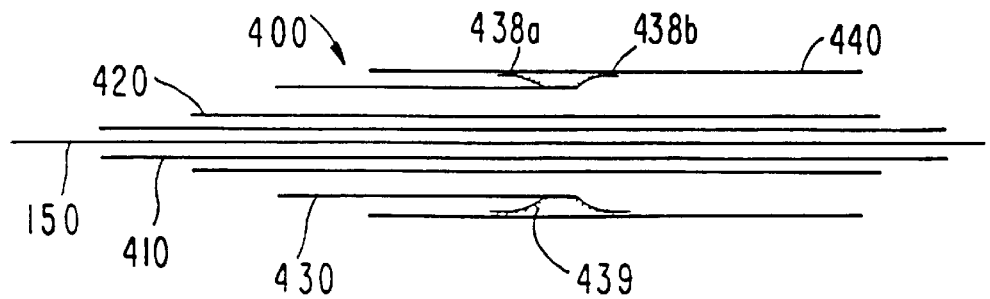
FIG. 17 is a simplified longitudinal sectional view of an illustrative embodiment of another portion of the FIG. 15 apparatus.

The portion of assembly 440 at which the proximal end of conduit 430 is located is shown in FIG. 17. There it will be seen how flaps 438 are confined within conduit delivery tube 440. FIG. 17 also shows how tubes 410, 420, and 440 extend proximally (to the right as viewed in FIG. 17) from the proximal end of conduit 430 so that the physician can remotely control the distal portion of assembly 400 from outside the patient.

Figure 18:
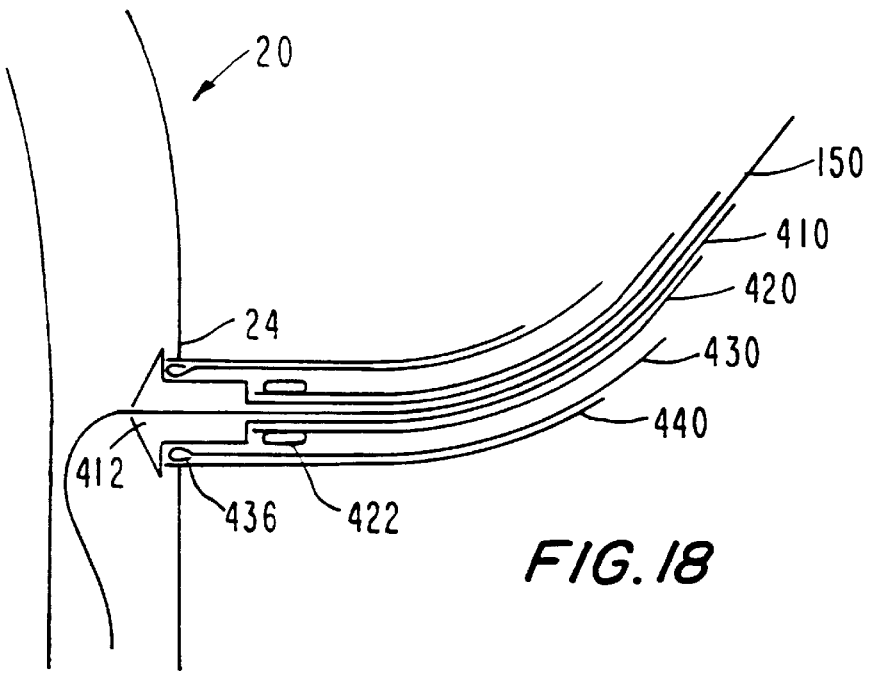
FIG. 18 is a view similar to a portion of FIG. 14 showing an even later stage in the illustrative procedure depicted in part by FIG. 14.

To install artificial graft conduit 430 in the patient between regions 24 and 34, assembly 400 is fed into the patient along wire 150 through catheter 210. When tip 412 reaches coronary artery portion 24, tip 412 is threaded into and through the coronary artery wall by rotating tube 410 and therefore tip 412. The passage of tip 412 through the coronary artery wall opens up the aperture previously made by wire 150 in that wall. After tip 412 passes through the artery wall, that wall seals itself against the outside of the distal portion of conduit delivery tube 440 as shown in FIG. 18.

Figure 19:
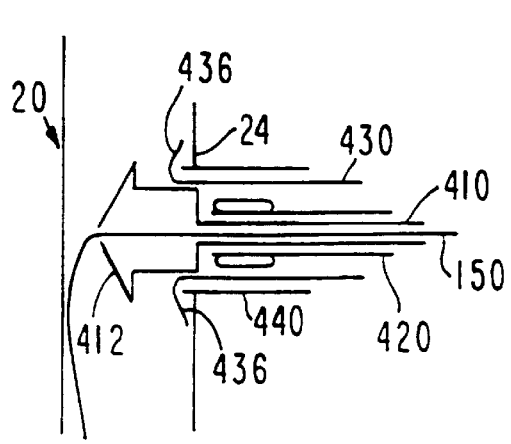
FIG. 19 is a view similar to FIG. 18 showing a still later stage in the FIG. 18 procedure.

The next step is to push tube 410 and tip 412 distally relative to delivery tube 440, which is held stationary. Conduit 430 is initially moved distally with components 410 and 412. This may be done by inflating balloon 422 so that it engages conduit 430, and then moving tube 420 distally with components 410 and 412. Distal motion of conduit 430 moves hooks 436 beyond the distal end of delivery tube 440, thereby allowing the hooks to spring out inside coronary artery 20 as shown in FIG. 19. This prevents the distal end of conduit 430 from being pulled proximally out of the coronary artery. If balloon 422 was inflated during this phase of the procedure, it may be deflated before beginning the next phase.

Figure 20:
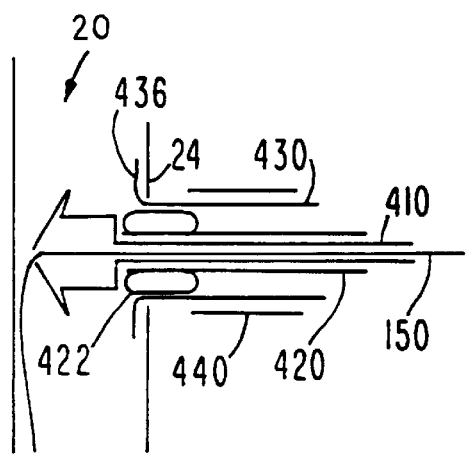
FIG. 20 is a view similar to FIG. 19 showing an even later stage in the FIG. 19 procedure.

The next step is to pull delivery tube 440 back slightly so that it is withdrawn from coronary artery 20. Then tube 420 is moved distally so that balloon 422 is radially inside the annulus of hooks 436. Balloon 442 is then inflated to ensure that hooks 436 are firmly set in coronary artery 20. Conditions are now as shown in FIG. 20. Cross sections of balloon 422 may be L-shaped when inflated (one leg of the L extending parallel to the longitudinal axis of conduit 430, and the other leg of the L extending radially outward from that longitudinal axis immediately distal of hooks 436). This may further help to ensure that hooks 436 fully engage the wall of coronary artery 20.

Figure 21:
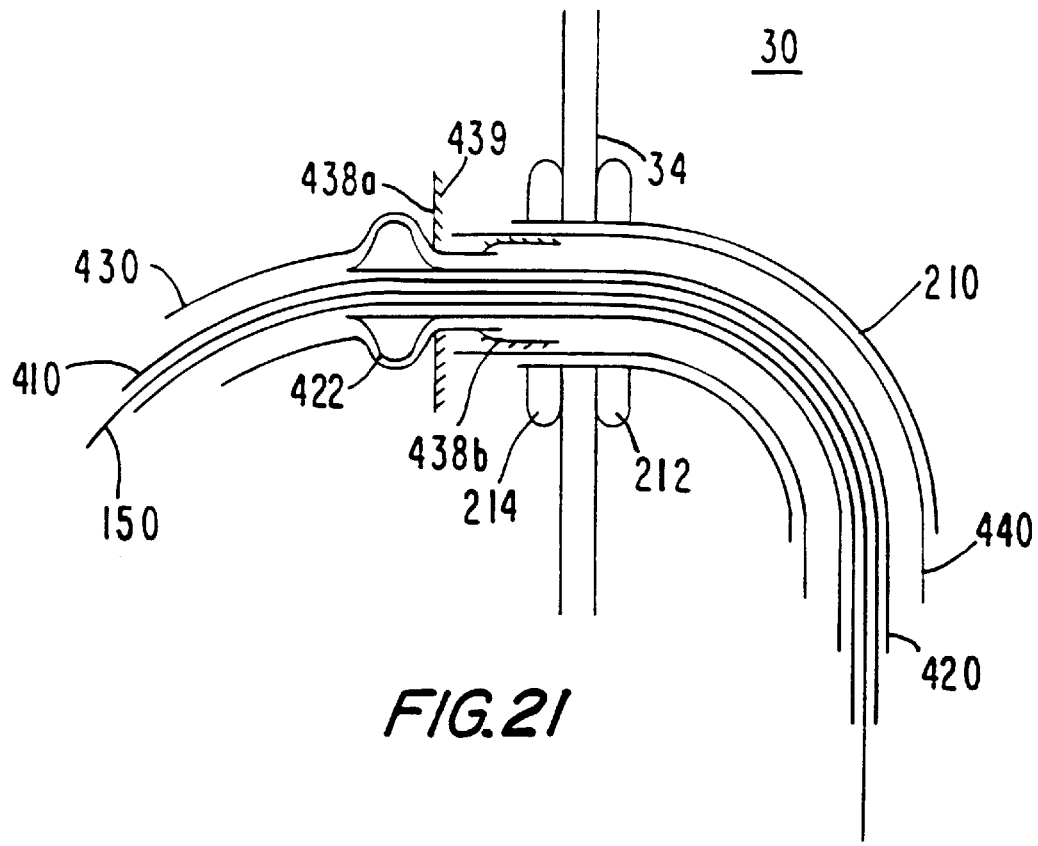
FIG. 21 is a view similar to another portion of FIG. 14 showing a still later stage in the FIG. 20 procedure.

The next step is to deflate balloon 422. Then delivery tube 440 is withdrawn proximally until flap 438a (but not flap 438b) is distal of the distal end of the delivery tube. This allows flap 438a to spring radially out as shown in FIG. 21. Tube 420 is then withdrawn until balloon 422 is just distal of flap 438a. Then balloon 422 is inflated, producing the condition shown in FIG. 21.

Figure 22:
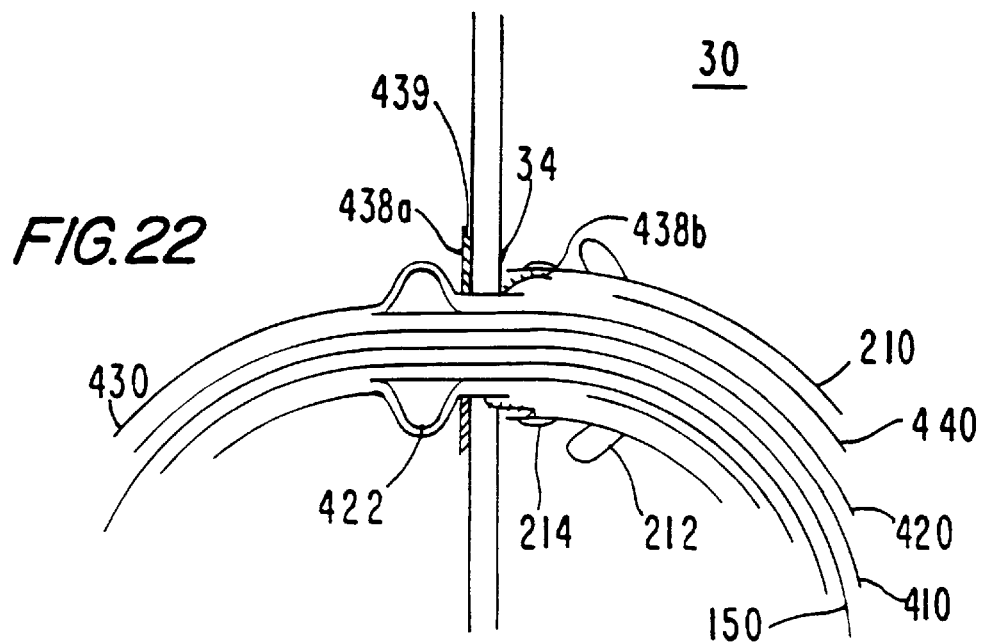
FIG. 22 is a view similar to FIG. 21 showing an even later stage in the FIG. 21 procedure.

The next steps are (1) to deflate distal balloon 214, (2) to proximally withdraw catheter 210 a short way, (3) to proximally withdraw tube 420 to press flap 438a against the outer surface of the aorta wall, and (4) to proximally withdraw delivery tube 440 by the amount required to allow flap 438b to spring out against the interior of catheter 210, all as shown in FIG. 22. As a result of the above-described proximal withdrawal of tube 420, the hooks or barbs 439 on flap 438a are urged to enter the aorta wall tissue to help maintain engagement between flap 438a and the wall of the aorta. Inflated balloon 422 helps to set hooks or barbs 439 in the tissue when tube 420 is tugged proximally.

Figure 22A:
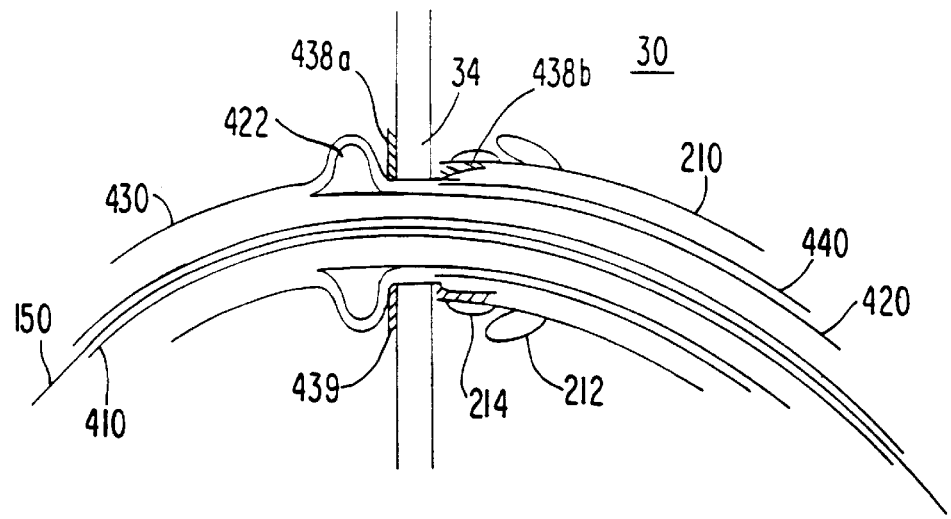
FIG. 22a is a view similar to FIG. 22 showing a still later stage in the FIG. 22 procedure.

The next step is to insert the distal portion of delivery tube 440 into the proximal end of conduit 430 as shown in FIG. 22a. The distal end of conduit 440 may be inserted all the way to the proximal end of balloon 422 (see FIG. 23 for a depiction of this). A purpose of this step is to subsequently help control the rate at which blood is allowed to begin to flow through conduit 430.

Figure 22B:
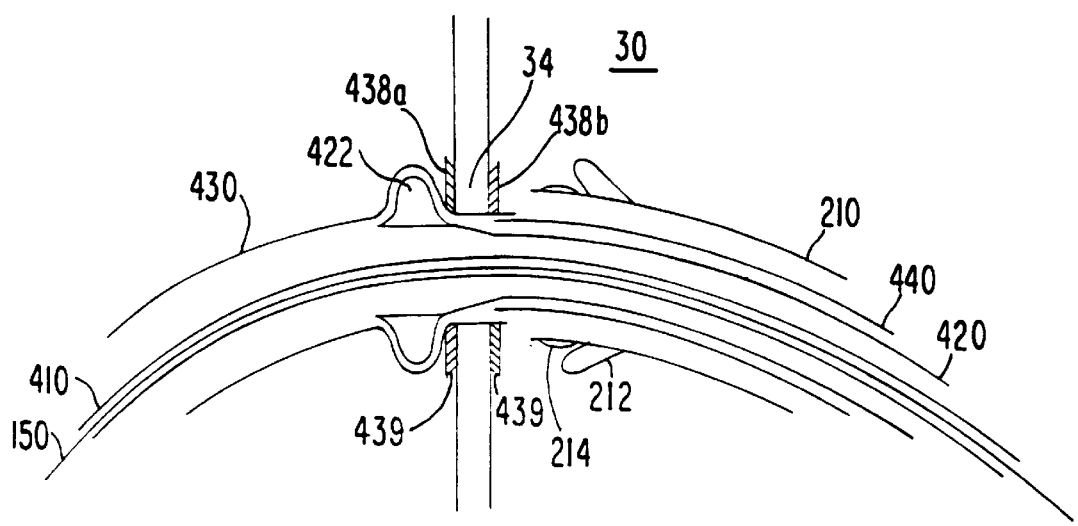
FIG. 22b is a view similar to FIG. 22a showing an even later stage in the FIG. 22a procedure.
Figure 23:
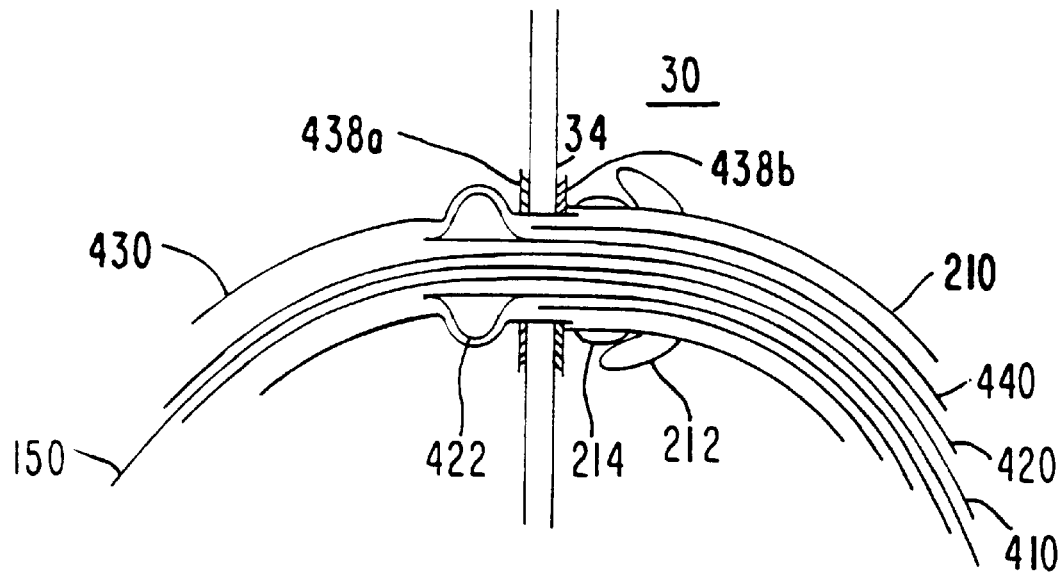
FIG. 23 is a view similar to FIG. 22b showing a still later stage in the FIG. 22b procedure.

The next step is to proximally withdraw catheter 210 by the amount required to release flap 438b to spring out against the interior of the wall of aorta 30 as shown in FIG. 22b. Catheter 210 may be subsequently pushed back against flap 438b as shown in FIG. 23 to help securely engage that flap against the aorta wall.

Figure 24:
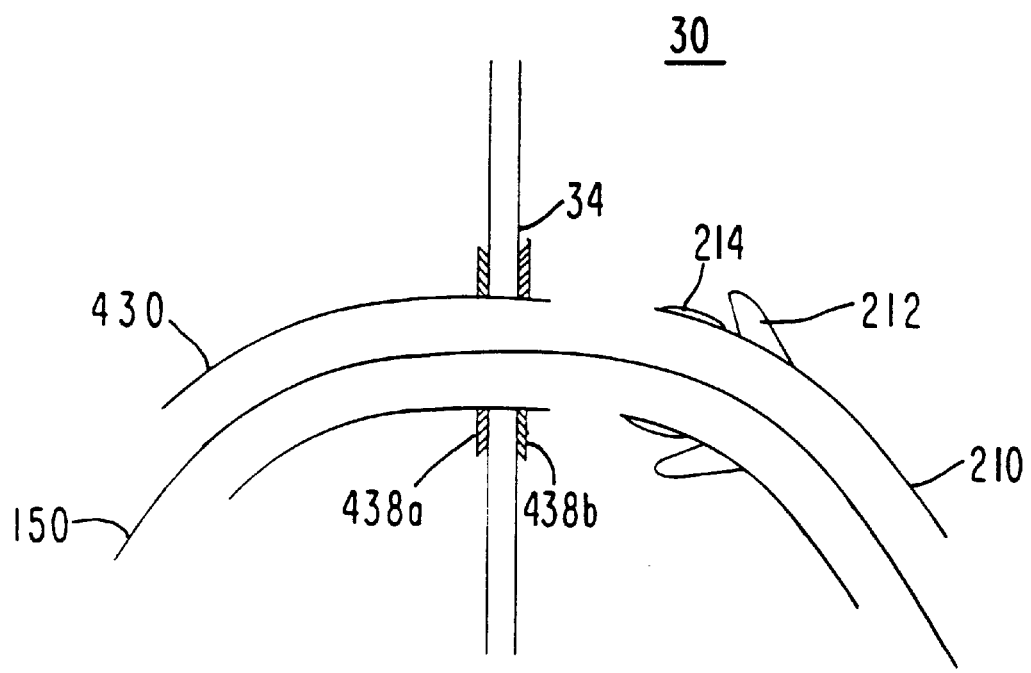
FIG. 24 is a view similar to FIG. 23 showing an even later stage in the FIG. 23 procedure.

Artificial graft conduit 430 is now fully established between aorta region 34 and coronary artery region 24. The next steps are therefore to deflate balloon 422 and proximally withdraw tube 420, to collapse tip 412 and proximally withdraw tube 410, and to proximally withdraw delivery tube 440. The proximal end of conduit 430 is now as shown in FIG. 24. As possible alternatives to what is shown in FIG. 24, the distal end of catheter 210 could be left pressed up against proximal flap 438b and/or the distal portion of delivery tube 440 could be left inside the proximal portion of conduit 430. If the latter possibility is employed, then delivery of the natural graft conduit (described below) can be through tube 440.

Figure 15A:
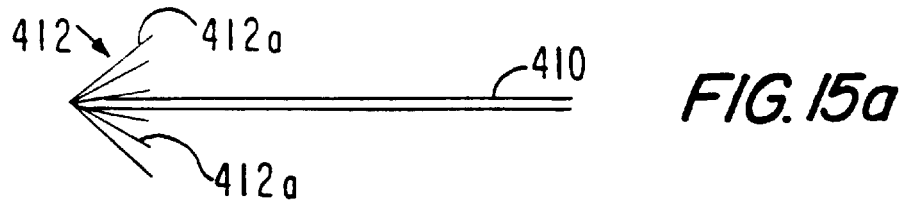
FIG. 15a is a simplified elevational view of a structure which can be used to provide part of the apparatus shown in FIG. 15.
Figure 15B:
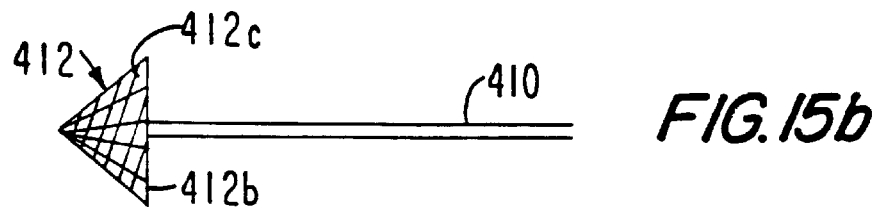
Figure 15C:
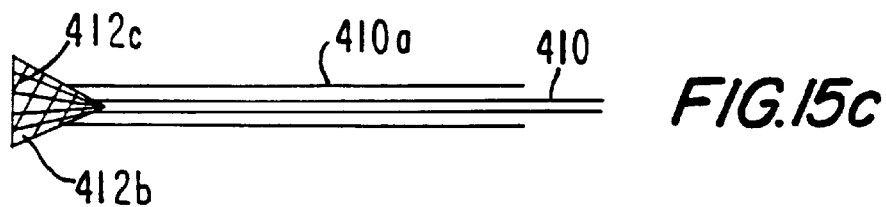
FIG. 15c is a view similar to FIG. 15b showing the FIG. 15b structure in another operational condition.

Several illustrative embodiments of collapsible tips 412 are shown in FIGS. 15a–15g. In the first embodiment (shown in FIGS. 15a–15c) a frame of wire struts 412a extends radially out and proximally back from the distal end of hypotube 410 (see especially FIG. 15a). This frame is covered with a somewhat elastic polymer cover 412b (FIG. 15b) which is provided with threads as indicated at 412c. For example, threads 412c may be made of one or more spirals of nitinol wire or other metal. When it is desired to collapse tip 412, another hypotube 410a (which is disposed around hypotube 410) is shifted distally relative to hypotube 410 to invert and collapse tip 412 as shown in FIG. 15c.

Figure 15D:
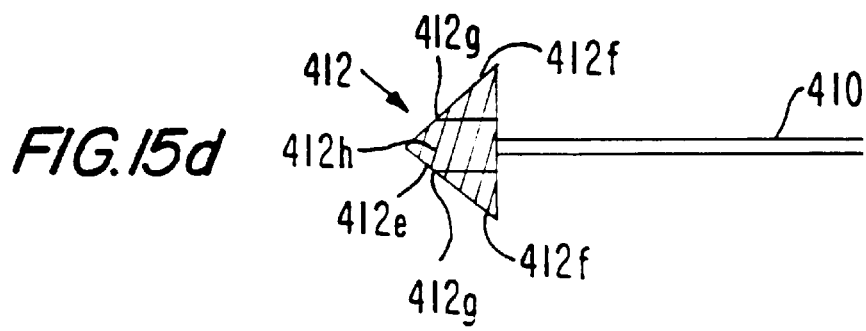
FIG. 15d is a simplified elevational view of an alternative structure which can be used to provide part of the apparatus shown in FIG. 15.
Figure 15E:
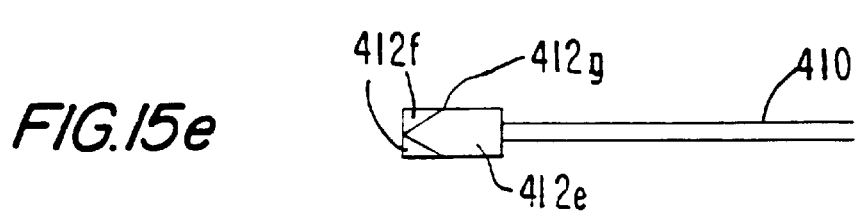
FIG. 15e is a view similar to FIG. 15d showing the FIG. 15d structure in another operational condition.

In the alternative embodiment shown in FIGS. 15d and 15e, tip 412 has a central main portion 412e attached to hypotube 410. Around the proximal portion of main portion 412e are a plurality of triangular shaped portions 412f, each of which is connected to main portion 412e by a hinge 412g. The outer surface of the tip is threaded as indicated at 412h. For example, in this embodiment tip 412 may be made of a plastic polymer material, and hinges 412g may be so-called "living" hinges between the various masses of the polymer. As soon as triangular portions 412f meet any resistance as tip 412 is withdrawn proximally, they pivot about their hinges 412g to the positions shown in FIG. 15e, thereby greatly reducing the circumferential size of the tip.

Figure 15F:
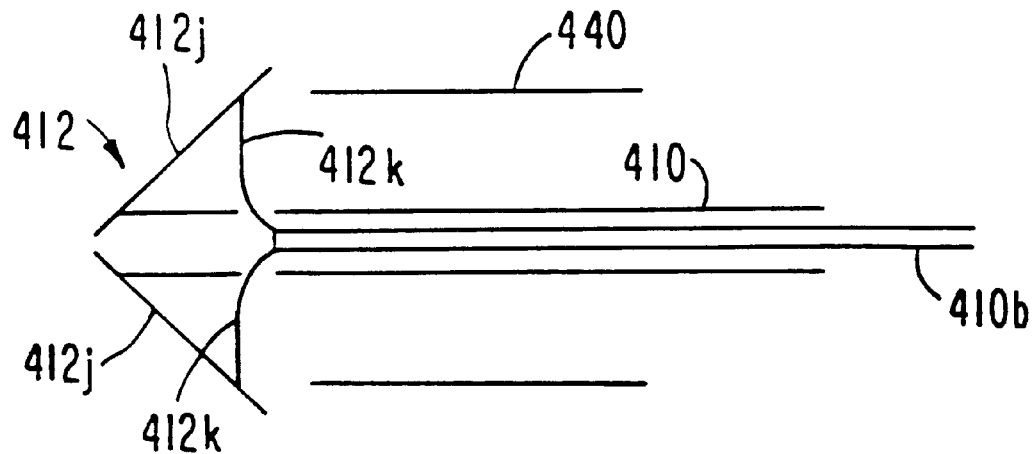
FIG. 15f is a simplified longitudinal sectional view of another alternative structure which can be used to provide part of the apparatus shown in FIG. 15.
Figure 15G:
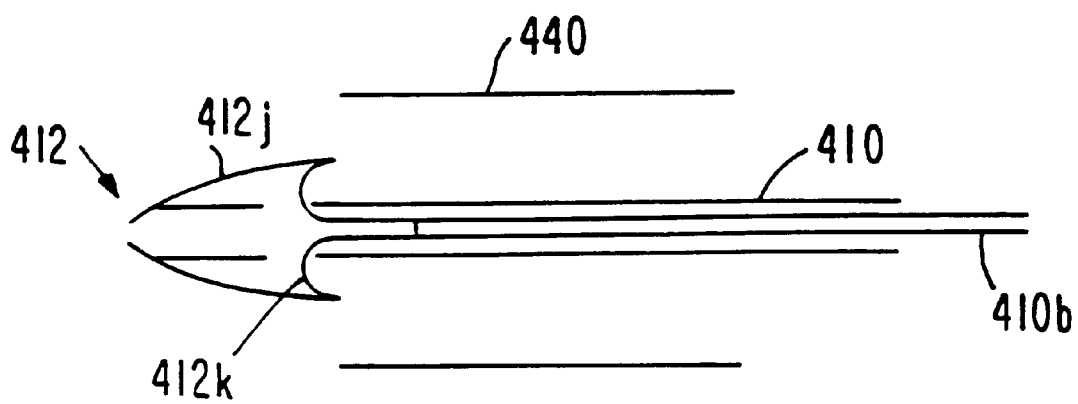
FIG. 15g is a view similar to FIG. 15f showing the FIG. 15f structure in another operational condition.

In the further alternative embodiment shown in FIGS. 15f and 15g, metal struts 412j are attached to the distal end of hypotube 410 so that they extend radially out and proximally back. Although not shown in FIGS. 15f and 15g, struts 412j are covered with a cover and threads like the cover 412b and threads 412c shown in FIG. 15b and described above. A wire 412k connects a proximal portion of each strut 412j, through an aperture in hypotube 410, to the distal end of another hypotube 410b which is disposed inside hypotube 410. When wires 412k are relaxed as shown in FIG. 15f, struts 412j extend radially out beyond the circumference of delivery tube 440. When it is desired to collapse tip 412, hypotube 410b is pulled back proximally relative to hypotube 410 as shown in FIG. 15g. This causes wires 412k to pull struts 412j in so that the outer circumference of tip 412 is much smaller than the circumference of delivery tube 440.

Again, it should be mentioned that the use of a threaded, collapsible tip 412 as described above is only one of several possibilities. Other alternatives are discussed below after completion of the discussion of the illustrative procedure which is being described and which will now be further considered with reference to FIG. 25 and subsequent FIGS.

As has been mentioned, the illustrative procedure being described assumes that natural body conduit (e.g. a length of the patient's saphenous vein that has been harvested for this purpose) is installed inside artificial conduit 430 after installation of the latter conduit. An illustrative assembly 500 for delivering a length of natural body conduit to installed conduit 430 is shown in FIG. 25.

Figure 25:
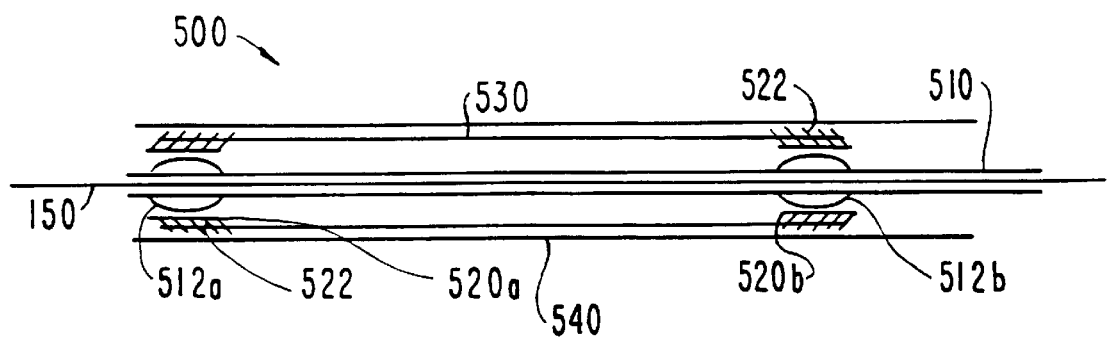
FIG. 25 is a simplified longitudinal sectional view of an illustrative embodiment of a portion of more apparatus in accordance with this invention.

As shown in FIG. 25, assembly 500 includes a tube 510 disposed around wire 150 so that tube 510 is freely movable in either direction along wire 150. Tube 510 has an inflatable annular balloon 512a near its distal end and another inflatable annular balloon 512b spaced in the proximal direction from balloon 512a. Tube 510 includes separate inflation lumens (not shown) for each of balloons 512 so that the balloons can be separately inflated and deflated. An annular collar structure or ring 520a is disposed concentrically around balloon 512a, and a similar annular collar structure or ring 520b is disposed concentrically around balloon 512b. Balloons 512 may be partly inflated. Each of rings 520 may have radially outwardly extending hooks or barbs 522. A length of natural body conduit 530 (e.g., saphenous vein as mentioned earlier) extends from ring 520a to ring 520b around the intervening portion of tube 510. Hooks or barbs 522 may extend through the portions of conduit 530 that axially overlap rings 520. A delivery tube 540 is disposed around conduit 530. In use, tubes 510 and 540 extend proximally (to the right as viewed in FIG. 25) out of the patient to permit the physician to remotely control the distal portion of assembly 500.

Although not shown in FIG. 25, assembly 500 may include a spring coil (similar to coil 450 in FIG. 36) extending between rings 520 inside of conduit 530 to help hold conduit 530 open and out against delivery tube 540 or subsequently out against conduit 430. Instead of balloons 512 being both in the same tube 510, balloon 512a may be on a relatively small first tube, while balloon 512b is on a larger second tube that concentrically surrounds the proximal portion of the first tube. The first and second tubes are axially movable relative to one another, thereby allowing the distance between balloons 512 to be adjusted for grafts 530 of different lengths. Illustrative apparatus of this kind is shown in Goldsteen et al. U.S. patent application Ser. No. 08/839,298, filed Apr. 17, 1997 (Docket No. 293/009), which is hereby incorporated by reference herein.

Figure 26:
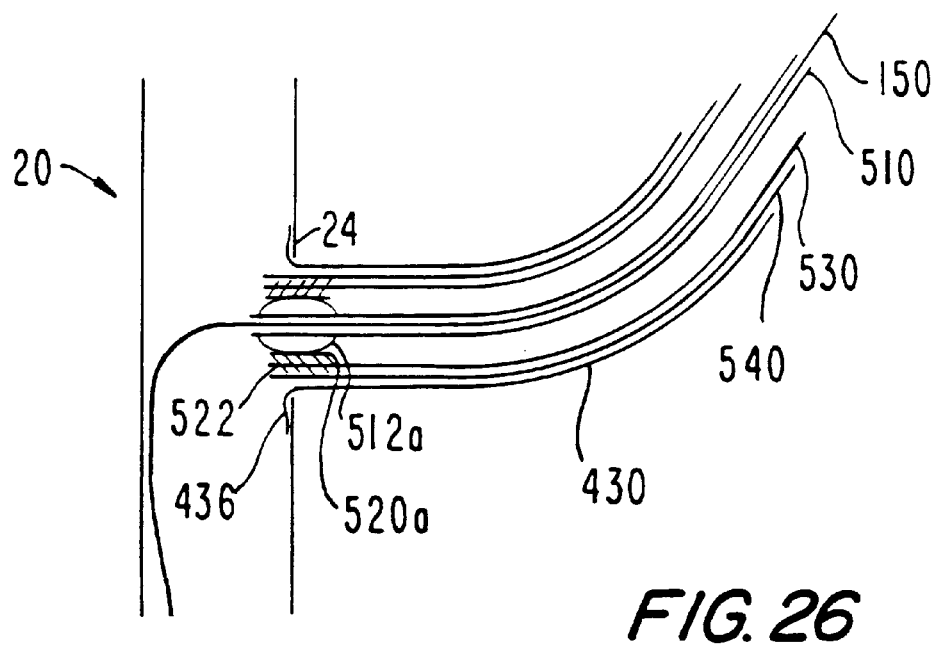
FIG. 26 is a view similar to FIG. 20 showing a later stage in the FIG. 24 procedure.
Figure 28:
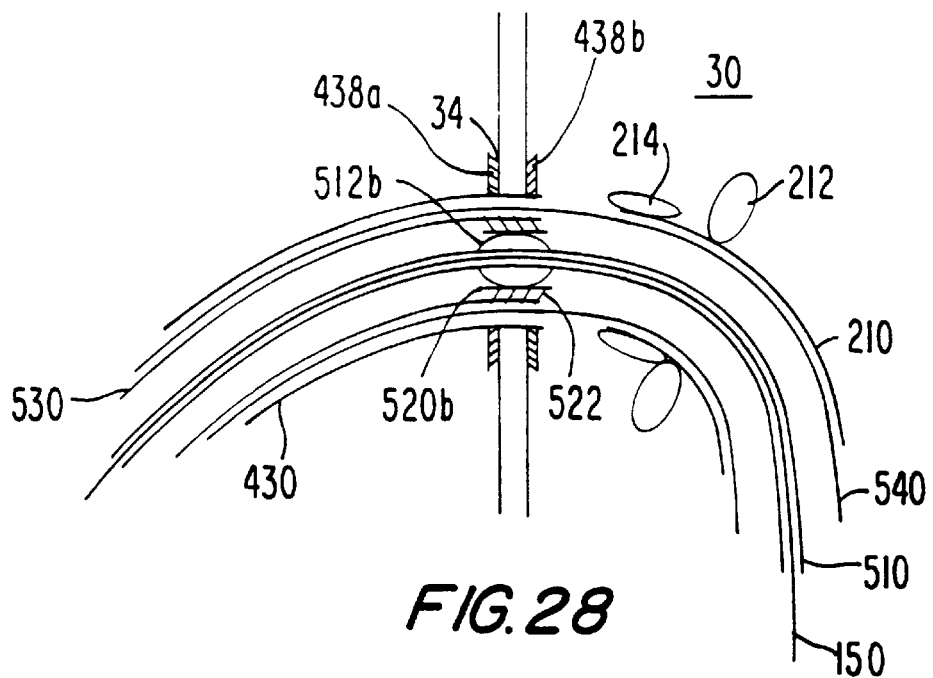
FIG. 28 is a view similar to FIG. 24 showing an even later stage in the FIG. 27 procedure.

Assembly 500 is employed by placing it on wire 150 leading into catheter 210. Assembly 500 is then advanced distally along wire 150 through catheter 210 and then into conduit 430 until the distal end of conduit 530 is adjacent the distal end of conduit 430 and the proximal end of conduit 530 is adjacent the proximal end of conduit 430. The condition of the apparatus at the distal end of assembly 500 is now as shown in FIG. 26. The condition of the apparatus at the proximal end of conduit 530 is as shown in FIG. 28.

Figure 27:
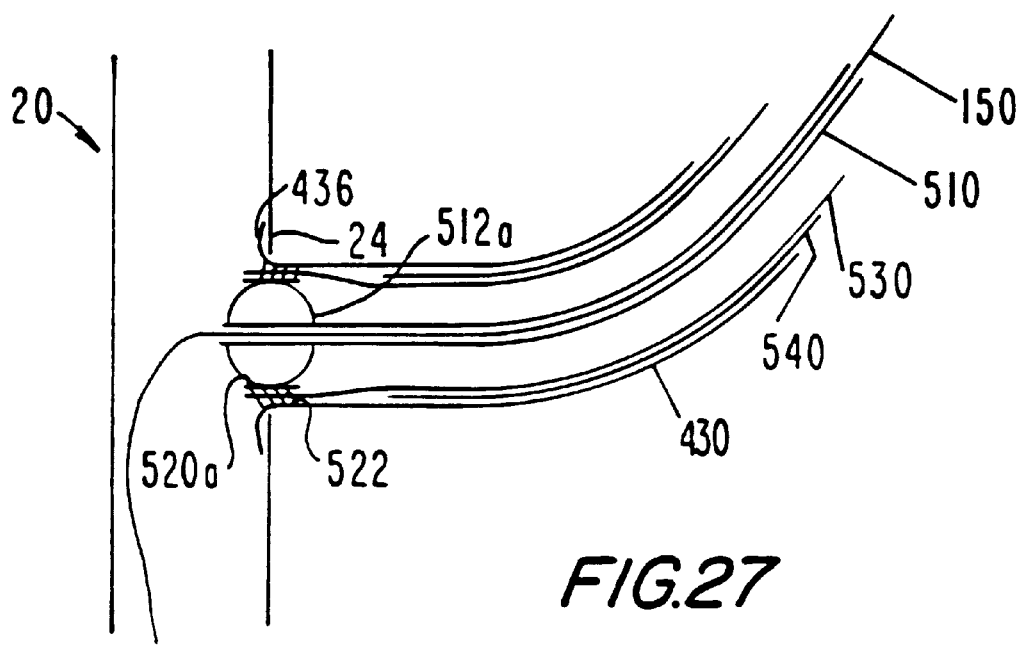
FIG. 27 is a view similar to FIG. 26 showing a still later stage in the FIG. 26 procedure.

The next step is to proximally withdraw delivery tube 540 so that the distal portion of conduit 530 and distal barbed ring 520a are no longer inside the distal portion of delivery tube 540. Then distal balloon 512a is inflated to circumferentially expand ring 520a and to set hooks or barbs 522 through conduit 530 into the surrounding portion of conduit 430 and coronary artery wall portion 24. This provides a completed anastomosis of the distal end of conduit 530 to coronary artery 20. FIG. 27 shows the condition of the apparatus at this stage in the procedure.

Figure 29:
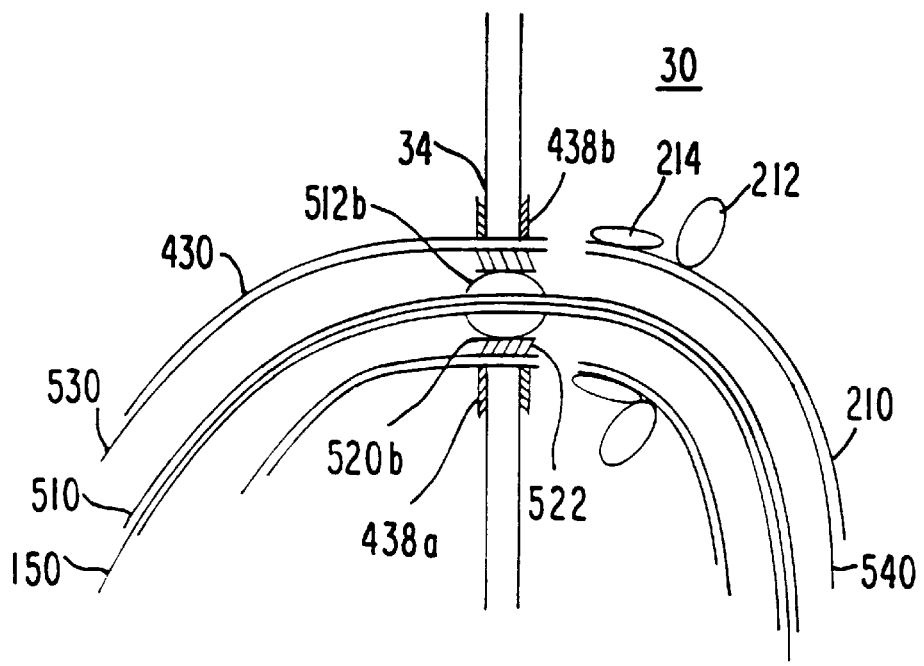
FIG. 29 is a view similar to FIG. 28 showing a still later stage in the FIG. 28 procedure.
Figure 30:
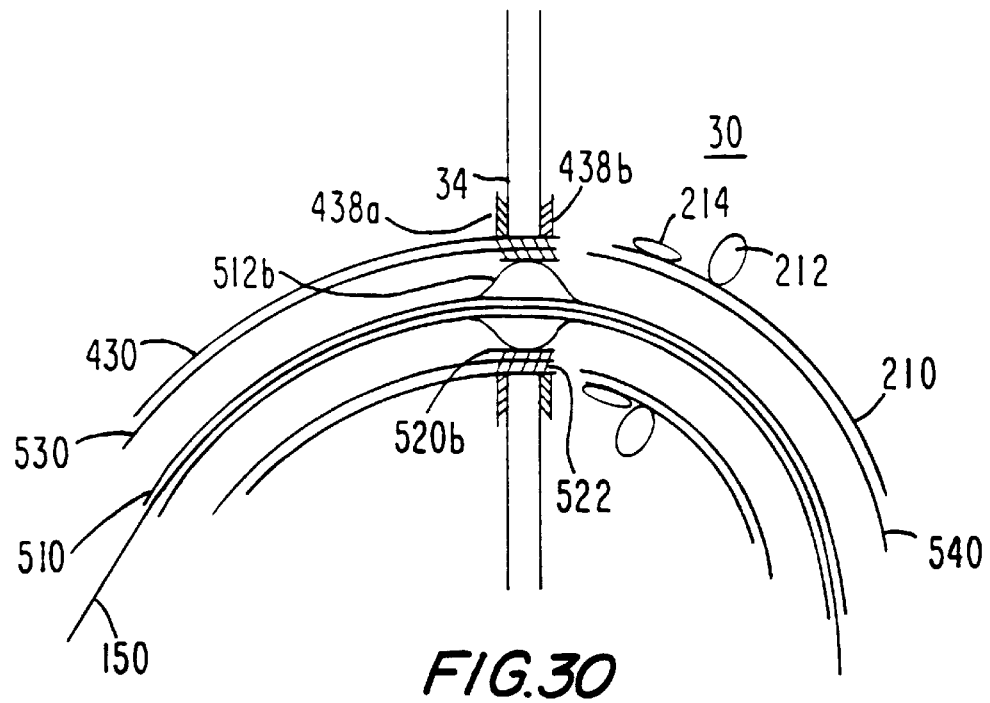
FIG. 30 is a view similar to FIG. 29 showing an even later stage in the FIG. 29 procedure.

The next step is to continue to proximally withdraw delivery tube 540 until the proximal end of conduit 530 and proximal ring 520b are no longer inside tube 540 (see FIG. 29). Then proximal balloon 512b is inflated to circumferentially expand ring 520b and thereby set hooks or barbs 522 through conduit 530 into the surrounding portion of conduit 430 and aorta wall portion 34 (see FIG. 30). This provides a completed anastomosis of the proximal end of conduit 530 to aorta 30.

Figure 31:
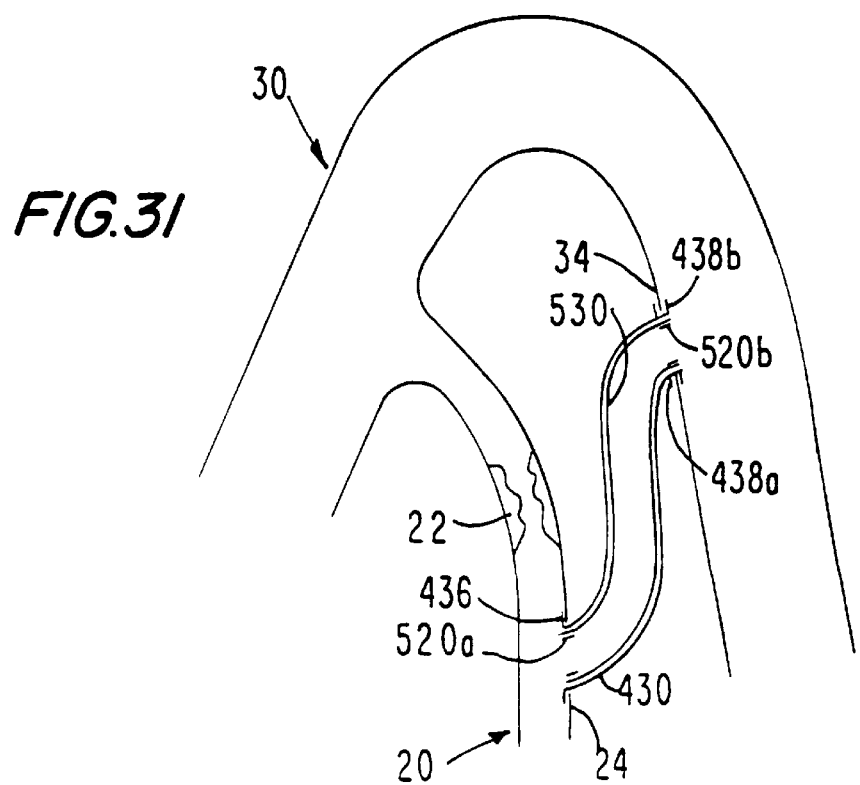
FIG. 31 is a view similar to FIG. 14 showing the end result of the procedure depicted in part by FIG. 30.

The next step is to deflate balloons 512a and 512b and proximally withdraw tube 510 and delivery tube 540 from the patient via catheter 210. Then wire 150 is withdrawn from the patient by pulling it proximally from catheter 210. Lastly, catheter 210 is proximally withdrawn from the patient to conclude the procedure. The bypass that is left in the patient is as shown in FIG. 31. This bypass extends from aorta 30 at location 34 to coronary artery 20 at location 24. The bypass includes natural body conduit 530 inside artificial graft conduit 430. One end of the bypass is anchored and anastomosed to coronary artery 20 by hooks 436 and ring 520a. The other end of the bypass is anchored and anastomosed to aorta 30 by flaps 438 and ring 520b.

Figure 32:
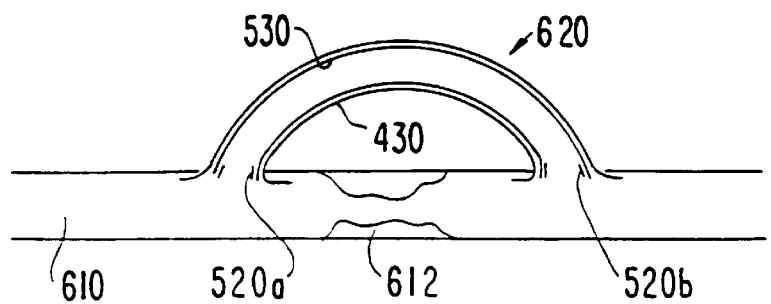
FIG. 32 is a simplified longitudinal sectional view showing an end result similar to FIG. 31 but in a different context.

The particular uses of the invention that have been described in detail above are only illustrative of many possible uses of the invention. Other examples include same-vessel bypasses in the coronary area and vessel-to-vessel and same-vessel bypasses in other portions of the circulatory system (including neurological areas, renal areas, urological areas, gynecological areas, and peripheral areas generally). A same-vessel bypass is a bypass that extends from one portion of a vessel to another axially spaced portion of the same vessel. In FIG. 32, bypass 620 is a same-vessel bypass around a narrowing 612 in vessel 610. For ease of comparison to previously described embodiments, the various components of bypass 620 are identified using the same reference numbers that are used for similar elements in FIG. 31. The invention is also applicable to procedures similar to any of those mentioned above, but for non-circulatory systems such as urological tubing.

Figure 33:
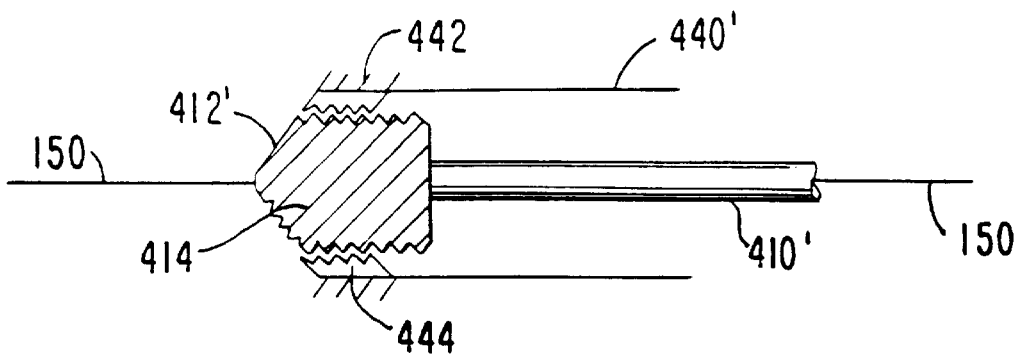
FIG. 33 is a simplified longitudinal sectional view showing a possible alternative construction of portions of the apparatus showing in FIG. 15.

It has been mentioned that the collapsible tip structures shown, for example, in FIGS. 15–15g are illustrative of only one of several possible approaches to providing a structure that can penetrate the wall of coronary artery 20 from outside the artery. Another example of a suitable structure is shown in FIG. 33. To facilitate comparison to FIG. 15, FIG. 33 uses reference numbers with primes for elements that are generally similar to elements identified by the corresponding unprimed reference numbers in FIG. 15.

In the embodiment shown in FIG. 33 distal tip 412' has external threads 414 for helping to grip and dilate tissue such as the wall of coronary artery 20 as tip 412' is rotated about wire 150 by rotation of proximally extending tubular shaft 410'. Threads 414 continue as threads 442 on the exterior of the distal portion of tube 440'. Threads 414 also threadedly engage with threads 444 on the interior of the distal portion of tube 440'. Thus when both of structures 410' and 440' are rotated together, threads 414 and 442 tend to pull tip 412' and then the distal portion of tube 440' into and through the wall of coronary artery 20. In the course of this, threads 412' transfer the tissue to threads 442. Thereafter, structure 410' can be removed from structure 440' by rotating structure 410' in the direction relative to structure 440' that causes threads 414 and 444 to cooperate to shift tip 412' proximally relative to structure 440'. When tip 412' has thus shifted proximally beyond threads 444, elements 410' and 412' can be pulled proximally out of the patient. Tube 440', which remains in place through the coronary artery wall, can thereafter be used as a guide tube for delivery of a graft structure (such as 430 (FIGS. 15–17)) and associated instrumentation (such as structure 420 (e.g., FIGS. 15 and 17)) to the operative site.

Figure 34:
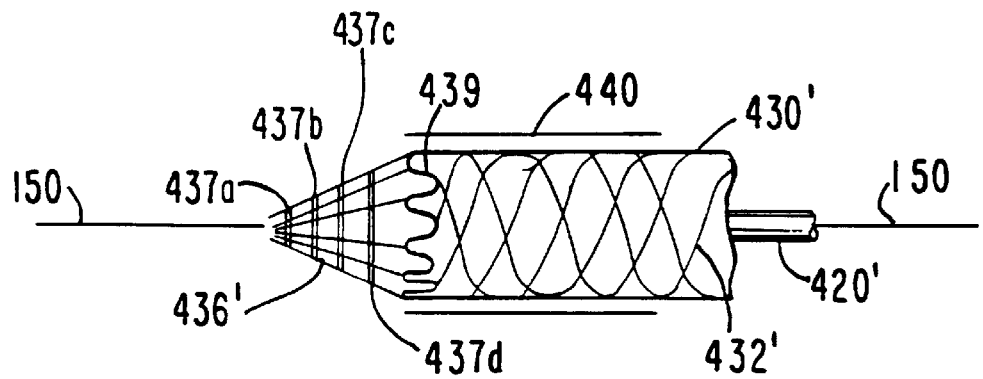
FIG. 34 is a simplified elevational view (partly in section) showing another possible alternative construction of portions of the FIG. 15 apparatus.
Figure 35:
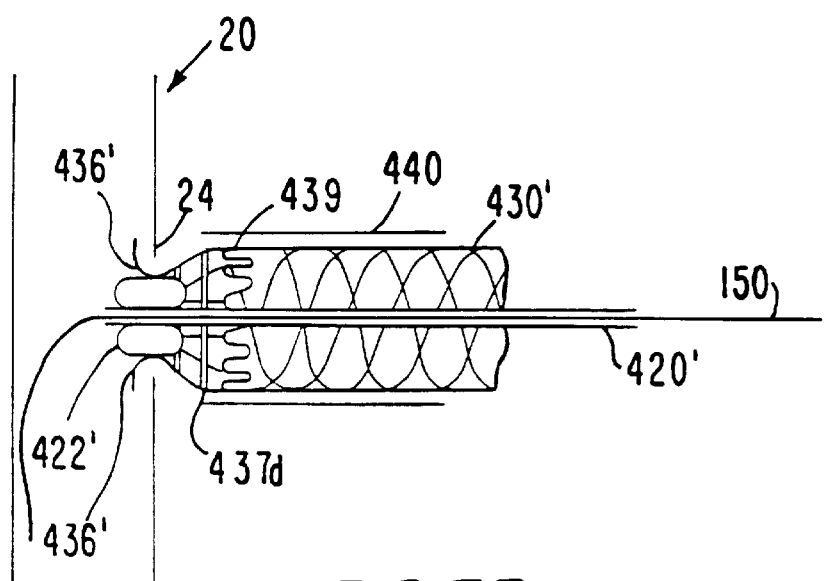
FIG. 35 is a simplified longitudinal sectional view of the FIG. 34 apparatus in another operating condition.

Another illustrative alternative embodiment of some of the instrumentation shown in FIG. 15 is shown in FIGS. 34 and 35. Once again, to facilitate comparison to FIG. 15, FIGS. 34 and 35 use reference numbers with primes for elements that are generally similar to elements identified by the corresponding unprimed reference numbers in FIG. 15. In the embodiment shown in FIGS. 34 and 35 struts 436' are connected to the distal end of a serpentine ring 439 which is connected in turn to the distal end of frame 432'. Struts 436' are initially held in the form of a distally pointed cone by yieldable bands 437a, 437b, 437c, and 437d. As elsewhere along graft conduit 430', the spaces between struts 436' are substantially filled by a highly elastic material such as silicone rubber. Bands 437 may be made of a polymeric or other suitable yieldable material. Alternatively, bands 437 could be serpentine metal members that yield by becoming straighter. Bands 437 are initially strong enough to prevent struts 436' from flaring radially outward from conduit 430' as the struts are resiliently biased to do. However, bands 437 can be made to yield by inflating balloon 422' (on the distal end of tube 420') inside the annulus of struts 436'.

Struts 436' can be forced through tissue such as the wall of coronary artery 20 in their initial cone shape. Sufficient pushing force can be applied to the cone of struts 436' in any of several ways. For example, tube 420' may be metal (e.g., stainless steel) hypotube which can transmit pushing force to the cone of struts 436' by inflating balloon 422' to trap the base of the cone between balloon 422' and tube 440. Additional pushing force may then also be applied via tube 440 itself.

When a sufficient portion of the height of the cone of struts 436' is through the coronary artery wall, balloon 422' is inflated inside the cone as shown in FIG. 35 to cause bands 437 to yield. This allows struts 436' to flare radially outward inside the coronary artery, thereby anchoring the distal end of conduit 430' to the artery. Bands 437 may be made progressively weaker in the distal direction to facilitate prompt yielding of distal bands such as 437a and 437b in response to relatively little inflation of balloon 422', whereas more proximal bands such as 437c and 437d do not yield until somewhat later in response to greater inflation of balloon 422'. This progression of yielding may help ensure that the annulus of struts flares out in the desired trumpet-bell shape of hooks inside the coronary artery.

FIGS. 34 and 35 illustrate the point that if the structure used to enlarge the initial hole (made by wire 150) through the wall of coronary artery 20 is sufficiently sharp, it may not be necessary to provide threads on and rotation of the structure. Instead, the hole-enlarging structure can simply be pushed through the coronary artery wall. This same principle applies to all embodiments of structures for penetrating the coronary artery wall and subsequently enlarging the opening in that wall (e.g., as in FIGS. 13, 15–15g, 33, and 36–39).

FIGS. 36 and 37 illustrate another possible use of a cone structure like that shown in FIGS. 34 and 35, as well as illustrating other possible aspects of the invention. These FIGS. illustrate a structure that can be used to deliver an artificial graft conduit, or a natural graft conduit, or both an artificial graft conduit and a natural graft conduit simultaneously (e.g., with the natural conduit coaxially inside the artificial conduit). In the particular case shown in FIGS. 36 and 37 it is assumed that only natural graft conduit is being delivered, but it will be readily apparent that artificial graft conduit could be substituted for or added outside the natural graft conduit.

In the embodiment shown in FIGS. 36 and 37 the cone of struts 436' is mounted on the distal end of a highly elastic coil spring 450. The proximal end of coil 450 is attached to ring 460. The cone of barbs 436' is provided with additional, relatively short, radially outwardly projecting hooks or barbs 436" near the proximal base of the cone. As shown in FIG. 37, hooks or barbs 436" extend into and/or through the distal portion of a length of graft tubing 530, which (as has been mentioned) is assumed in this case to be natural body organ tubing such as saphenous vein. Ring 460 is similarly provided with radially outwardly extending hooks or barbs 462 which extend into and/or through the proximal portion of graft conduit 530. Ring 460 also includes resilient radially outwardly extending annular flaps 438a and 438b with hooks or barbs 439, all similar to correspondingly numbered elements in FIG. 16. Spring 450, which is inside conduit 530 between the cone of barbs 436' and ring 460, helps to support and hold open the graft conduit. Structure 420' (similar to structure 420' in FIGS. 34 and 35 and including balloon 422' as shown in those FIGS.) is disposed around wire 150 inside structures 436', 450, 460, and 530. Delivery tube 440 is disposed around conduit 530.

The embodiment shown in FIGS. 36 and 37 illustrates a structure which can be used to deliver and install natural body organ conduit without any full length artificial graft conduit being used. In a manner similar to what is shown in FIGS. 34 and 35, the structure shown in FIG. 37 is delivered to the operative site via wire 150. The cone of struts 436' is forced through the wall of coronary artery 20 and then flared radially outward inside the coronary artery to anchor the distal end of the graft conduit to that artery. The distal end of delivery tube 440 is pulled back as needed to aid in attachment of the distal end of the graft structure. Attachment of the proximal end of the graft structure to the wall of aorta 30 is performed similarly to what is shown in FIGS. 21–24. Accordingly, with distal flap 438a just outside the wall of aorta 30, delivery tube 440 is pulled back proximally to expose that flap. Flap 438a is thereby released to spring out and engage the outer surface of the aorta wall. After that has occurred, proximal flap 438b is adjacent the inner surface of the aorta wall. Tube 440 is pulled back proximally even farther to expose flap 438b so that it can spring out and engage the inner surface of the aorta wall. Natural body organ graft 530 is now fully installed in the patient. Structures 436', 450, and 460 remain in place in the patient to help anchor the ends of graft conduit 530 and to help hold open the medial portion of that conduit.

In embodiments like FIGS. 36 and 37, coil 450 is optional. If coil 450 is used, its ends may or may not be attached to structures 436 and/or 460.

A coil like coil 450 can be used in other embodiments of the invention. For example, a coil like 450 could be used between rings 520a and 520b in embodiments like that shown in FIG. 25 to help hold open graft conduit 530 in that embodiment.

Figure 38:
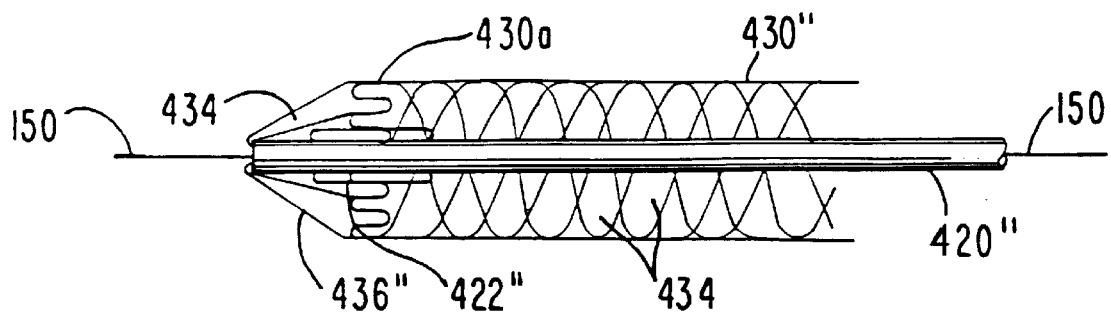
FIG. 38 is a simplified longitudinal sectional view showing still another possible alternative construction of portions of the FIG. 15 apparatus.

Still another illustrative alternative embodiment of some of the instrumentation shown in FIG. 15 is shown in FIG. 38. To facilitate comparison to FIG. 15, FIG. 38 uses reference numbers with double primes for elements that are generally similar to elements identified by the corresponding unprimed reference numbers in FIG. 15. In the embodiment shown in FIG. 38, the distal end of artificial graft conduit 430" is attached to expandable ring 430a. Elongated struts 436" extend distally from the distal end of ring 430a. The distal ends of struts 436" are turned back in the proximal direction and extend just far enough into the distal end of tube 420" to be releasably retained by that tube. Struts 436" are resiliently biased to extend radially outward from ring 430a, but are initially restrained from doing so by the presence of their distal end portions in the distal end of tube 420". Thus struts 436" initially form a distally pointing cone that can be pushed through tissue such as the wall of coronary artery 20 in the same manner that has been described above in connection with FIGS. 34–37. Structure 420", which may be metal (e.g., stainless steel) hypotube with an inflatable annular balloon 422" near its distal end, may be used to help push the cone through the tissue.

Figure 39:
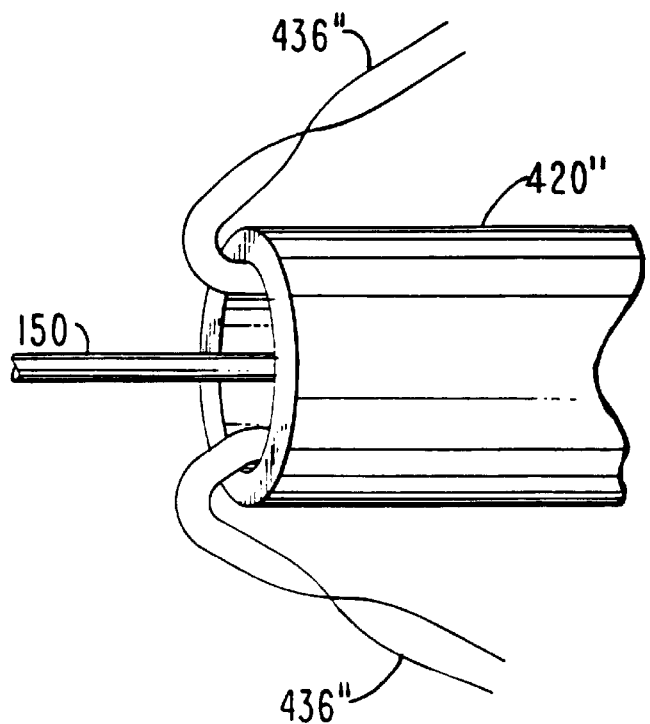
FIG. 39 is a simplified elevational view showing in more detail a possible construction of a portion of the FIG. 38 apparatus.

After the distal portion of the cone of struts 436" has been pushed through the wall of coronary artery 20, tube 420" is shifted proximally relative to the struts to release the distal end portions of the struts. This allows struts 436" to spring radially outward from ring 430a inside coronary artery 20, thereby anchoring the distal end of the graft conduit in the coronary artery. Ring 430a can then be circumferentially expanded to increase the size of the connection between coronary artery 20 and the distal portion of the graft conduit. If desired, each of struts 436" may be twisted 180° as shown in FIG. 39 before it enters the distal end of tube 420". This promotes turning of the extreme distal end portions of the struts toward the coronary artery wall when the struts are released from tube 420".

Ring 430a and struts 436" may be made of any suitable material such as any 300-series stainless steel (e.g., 316L stainless steel). Another material that may be suitable for struts 436" is nitinol. As in previously described embodiments, the elastic cover 434 that forms part of conduit 430" preferably extends to regions 430a and 436".

The structures shown herein and described above for penetrating existing body organ tissue for connecting and/or fastening graft structures to existing body organ tissues are only illustrative of structures that can be used. Other examples of such structures are shown in Bachinski et al. U.S. patent application Ser. No. 08/839,199, filed Apr. 23, 1997 (Docket No. 293/008), which is hereby incorporated by reference herein.

Although it has been said that it is not necessary in accordance with and for purposes of this invention to intralumenally approach more than one end of the graft site, it is not inconsistent with this invention to also use other instrumentation to intralumenally approach the other end of the graft site. For example, it may be desirable to introduce a catheter into coronary artery 20 during the procedure described above that includes FIG. 1 and related FIGS. in order to medicate the coronary artery, to introduce radiologic (e.g., fluroscopic) liquids into the coronary artery, etc.

Figure 40:
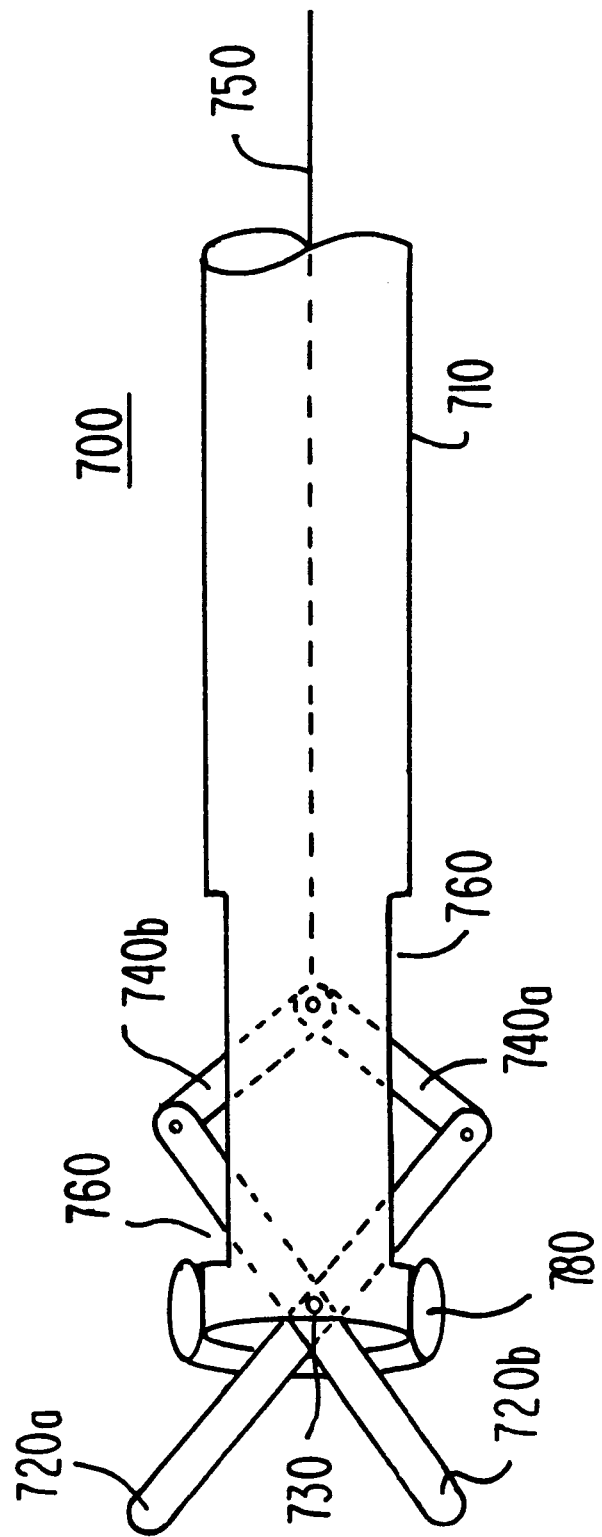
FIG. 40 is a simplified elevational view of illustrative apparatus that can be used as an alternative to certain apparatus shown in other FIGS.

FIG. 40 shows a structure 700 that may be used as an alternative to an inflatable balloon for radially enlarging a surrounding structure such as a connector between a natural or artificial graft and a patient's body tissue. For example, structures like structure 700 may be used in place of one or more of balloons 422 (FIGS. 15 and 18–23), 512a/512b (FIGS. 25–30), 422' (FIG. 35), or 422" (FIG. 38), or wherever else a generally similar radially enlargeable structure is needed.

Structure 700 includes an outer tube 710 (e.g., of metal hypotube). Near the distal end of tube 710 pivotable members 720a and 720b are pivotally mounted on a pin 730 which extends transversely across tube 710. The proximal portions of members 710a and 710b are pivotally connected to links 740a and 740b, respectively. The proximal ends of links 740 are pivotally connected to the distal end of wire 750. Axially extending slots 760 are formed in diametrically opposite sides of tube 710 to allow members 720 and 740 to extend radially out of tube 710, for example, as shown in FIG. 40. The distal ends of members 720 can be brought together by pulling wire 750 proximally relative to tube 710. Alternatively, that portion of structure 700 can be radially enlarged (i.e., the distal portions of members 720 can be spread apart) by pushing wire 750 distally relative to tube 710. Structure 700 is therefore another example of a selectively radially enlargeable structure that can be used in accordance with this invention.

If desired, one or more selectively inflatable balloons 780 may be disposed on structure 700. Each such balloon 780 preferably extends annularly around structure 700. (For greater clarity FIG. 40 only shows the rear half of annular balloon 780.) Balloon 780 and/or similar balloons may be used for such purposes as helping to hold a graft in position around structure 700 during use of structure 700 to transport the graft. Balloon 780 or like balloons may be selectively inflated via an inflation lumen which extends proximally from the balloon along component 710.

As an alternative to pushing wire 750 to spread the distal portions of members 720 apart, links 740 can start out more nearly partly overlapping the proximal portions of members 720. Then when wire 750 is pulled proximally relative to tube 710, the distal portions of members 720 will be spread apart.

It will be understood that the foregoing is only illustrative of the principles of the invention, and that various modifications can be made by those skilled in the art without departing from the scope and spirit of the invention. For example, the order of some steps in the procedures that have been described are not critical and can be changed if desired. The manner in which radiologic elements and techniques are used for observation of the apparatus inside the patient may vary. For example, radiologic fluids may be injected into the patient through various lumens in the apparatus to help monitor the location of various apparatus components in the patient, and/or radiologic markers (of which the above-described markers such as 154 and 206 are examples) may be provided anywhere on the apparatus that may be helpful to the physician.

The invention claimed is:

1. A method for installing a tubular graft between first and second spaced locations in a patient's tubular body structure comprising:

inserting an elongated structure into and along a lumen of the tubular body structure so that a distal portion of the elongated structure extends to the first location;

using a distal portion of the elongated structure to make a first aperture through the tubular body structure at the first location;

extending a distal portion of the elongated structure out of the first aperture and to the second location;

using a distal portion of the elongated structure to make a second aperture through the tubular body structure at the second location;

passing the graft along a lumen of the tubular body structure and then out one of said apertures to the other of said apertures; and attaching axially spaced portions of the graft to the tubular body structure adjacent the first and second locations.

2. The method defined in claim 1 wherein the elongated structure includes an elongated member which enters the tubular body structure via the second aperture, and wherein the passing includes:

disposing the graft around the elongated member so that the graft can follow the elongated member into the tubular body structure via the second aperture.

3. The method defined in claim 1 wherein the elongated structure includes an axially extending lumen which opens out at a distal portion of the elongated structure, and wherein said passing includes:

disposing the graft in the axially extending lumen.

4. The method defined in claim 1 further comprising:

withdrawing the elongated structure from the tubular body structure after performing the attaching.

5. The method defined in claim 1 wherein the attaching includes:

creating a substantially fluid-tight seal between the graft and the tubular body structure adjacent each of the first and second locations.

6. The method defined in claim 1 wherein the using a distal portion of the elongated structure to make a second aperture includes:

piercing the tubular body structure at the second location with a distal end of an elongated member.

7. The method defined in claim 6 wherein the distal end of the elongated member is threaded, and wherein the piercing includes:

rotating the elongated member about its longitudinal axis to cause the threads to threadedly engage the tubular body structure and pull the elongated member into the tubular body structure.

8. The method defined in claim 6 wherein the using a distal portion of the elongated structure to make a second aperture further includes:

feeding a distal portion of the elongated member into and along a lumen of the tubular body structure adjacent the second location.

9. The method defined in claim 6 wherein the using a distal portion of the elongated structure to make a second aperture includes:

radially expanding the aperture made by the piercing.

10. The method defined in claim 9 wherein the radially expanding includes:

inserting an enlarging structure into the aperture made by the piercing.

11. The method defined in claim 10 wherein the enlarging structure substantially concentrically surrounds the elongated member.

12. The method defined in claim 10 wherein the passing includes:

following the enlarging structure into the second aperture with an axial portion of the graft.

13. The method defined in claim 1 wherein the using of a distal portion of the elongated structure to make a second aperture includes:

piercing the tubular body structure at the second location with a distal portion of the elongated structure; and distally extending an elongated member from the distal portion of the elongated structure through the piercing and into the lumen of the tubular body structure adjacent the second location.

14. The method defined in claim 13 wherein the distally extending includes:

further extending a distal portion of the elongated member along the lumen of the tubular body structure leading away from the second location.

15. The method defined in claim 14 wherein the distal portion of the elongated member is threaded and wherein said further extending comprises:

rotating the elongated member about its longitudinal axis to cause threads on the distal portion of the elongated member to threadedly engage the interior of the lumen into which the distal portion of the elongated member is extended.

16. The method defined in claim 13 wherein the using of a distal portion of the elongated structure to make a second aperture includes:

radially enlarging the aperture made by the piercing.

17. The method defined in claim 16 wherein the radially enlarging includes:

inserting an enlarging structure into the aperture made by the piercing.

18. The method defined in claim 17 wherein the enlarging structure substantially concentrically surrounds the elongated member.

19. The method defined in claim 17 wherein the passing includes:

following the enlarging structure into the second aperture with an axial portion of the graft.

20. The method defined in claim 1 wherein the attaching includes:

radially expanding the graft inside the tubular body structure adjacent the second aperture to help prevent the graft from being pulled out of the second aperture.

21. The method defined in claim 1 wherein the attaching includes:

radially expanding the graft inside the tubular body structure adjacent the first aperture to help prevent the graft from being pulled out of the first aperture.

22. The method defined in claim 1 wherein the attaching includes:

extending hooks from the graft into the tubular body structure around the second aperture.

23. The method defined in claim 1 wherein the attaching includes:

extending hooks from the graft into the tubular body structure around the first aperture.

24. The method defined in claim 1 wherein in the passing the one of said apertures is the first aperture and the other of said apertures is the second aperture.

* * * * *